(12) United States Patent
Deck

(10) Patent No.: US 10,737,021 B2
(45) Date of Patent: Aug. 11, 2020

(54) CARTRIDGE AND INSERTER FOR A MEDICAL SYSTEM

(71) Applicant: ROCHE DIABETES CARE, INC., Indianapolis, IN (US)

(72) Inventor: Frank Deck, Niederkirchen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 26 days.

(21) Appl. No.: 15/821,482

(22) Filed: Nov. 22, 2017

(65) Prior Publication Data

US 2018/0093038 A1   Apr. 5, 2018

Related U.S. Application Data

(63) Continuation of application No. PCT/EP2016/061860, filed on May 25, 2016.

(30) Foreign Application Priority Data

May 26, 2015   (EP) .................................. 15169214

(51) Int. Cl.
*A61M 5/162* (2006.01)
*A61M 5/142* (2006.01)
*A61M 5/158* (2006.01)

(52) U.S. Cl.
CPC ........ *A61M 5/162* (2013.01); *A61M 5/14248* (2013.01); *A61M 5/158* (2013.01);
(Continued)

(58) Field of Classification Search
CPC .......... A61M 5/14244; A61M 5/14248; A61M 5/158; A61M 5/128; A61M 5/162;
(Continued)

(56) References Cited

U.S. PATENT DOCUMENTS 7,815,607 B2   10/2010   Rutti et al.
7,879,010 B2   2/2011   Hunn et al.
(Continued)

FOREIGN PATENT DOCUMENTS

CN   103300866 A   9/2013
CN   103781422 A   5/2014
(Continued)

OTHER PUBLICATIONS

International Search Report and Written Opinion of the ISA, PCT/EP2016/061860, dated Sep. 14, 2016, 17 pages.
(Continued)

*Primary Examiner* — Quynh-Nhu H. Vu
(74) *Attorney, Agent, or Firm* — Bose Mckinney & Evans LLP

(57) ABSTRACT

Disclosed is a medical system having a cartridge and an inserter. The cartridge includes a housing having an interior volume with a first guide within the interior volume. A cradle is disposed within the interior volume and is configured for mounting a medical appliance. The cradle includes a subcutaneous element and an insertion needle. The insertion needle is configured for being actuated to insert the subcutaneous element into a subject. The inserter includes a second guide configured to mate with the housing of the cartridge, and the first guide and second guide are configured to cooperate to guide the inserter into the interior volume along a guiding path defined by the first guide. The inserter is configured to removably attach to the cradle when guided into the interior volume. An insertion assembly is provided for actuating the insertion needle to insert the subcutaneous element into the subject.

10 Claims, 23 Drawing Sheets

(52) U.S. Cl.
CPC .............. *A61M 2005/14252* (2013.01); *A61M 2005/1585* (2013.01); *A61M 2005/1586* (2013.01); *A61M 2205/123* (2013.01); *A61M 2210/04* (2013.01)

(58) Field of Classification Search
CPC ........... A61M 2005/14252; A61M 2005/1585; A61M 2005/1586; A61M 2205/123; A61M 2210/04

See application file for complete search history.

(56) References Cited

U.S. PATENT DOCUMENTS

| | | | |
|---|---|---|---|
| 8,439,838 | B2 | 5/2013 | Mogensen et al. |
| 8,696,570 | B2 | 4/2014 | Yodfat et al. |
| 2004/0133164 | A1 | 7/2004 | Funderburk et al. |
| 2005/0101932 | A1* | 5/2005 | Cote ..................... A61M 5/158 604/506 |
| 2005/0119611 | A1 | 6/2005 | Marano-Ford et al. |
| 2005/0215979 | A1 | 9/2005 | Kornerup et al. |
| 2006/0095003 | A1 | 5/2006 | Marano-Ford et al. |
| 2006/0095014 | A1 | 5/2006 | Ethelfeld |
| 2006/0183984 | A1 | 8/2006 | Dabbles et al. |
| 2008/0009805 | A1 | 1/2008 | Ethelfeld |
| 2008/0039794 | A1 | 2/2008 | Kornerup et al. |
| 2008/0275407 | A1 | 11/2008 | Scheurer |
| 2008/0319414 | A1* | 12/2008 | Yodfat ................. A61B 5/6849 604/506 |
| 2009/0163874 | A1 | 6/2009 | Krag et al. |
| 2009/0254041 | A1 | 10/2009 | Krag et al. |
| 2011/0060289 | A1 | 3/2011 | Ethelfeld |
| 2011/0152778 | A1 | 6/2011 | Gyrn |
| 2012/0190951 | A1 | 7/2012 | Curry et al. |
| 2014/0088550 | A1 | 3/2014 | Bené et al. |
| 2014/0187876 | A1 | 7/2014 | Ohkoshi |

FOREIGN PATENT DOCUMENTS

| | | |
|---|---|---|
| DE | 102004039408 A1 | 3/2006 |
| EP | 1 475 113 A1 | 11/2004 |
| EP | 2046419 A1 | 4/2009 |
| EP | 2552513 B1 | 3/2014 |
| WO | WO 2006/077262 A1 | 7/2006 |
| WO | WO 2007/031126 A1 | 3/2007 |
| WO | WO 2010/003885 A1 | 1/2010 |
| WO | WO 2010/003886 A1 | 1/2010 |
| WO | WO 2010/034830 A1 | 4/2010 |
| WO | WO 2012/108959 A1 | 8/2012 |
| WO | WO 2013/178501 A1 | 12/2013 |

OTHER PUBLICATIONS

International Preliminary Report on Patentability, PCT/EP2016/061860, dated Nov. 28, 2017, 9 pages.

* cited by examiner

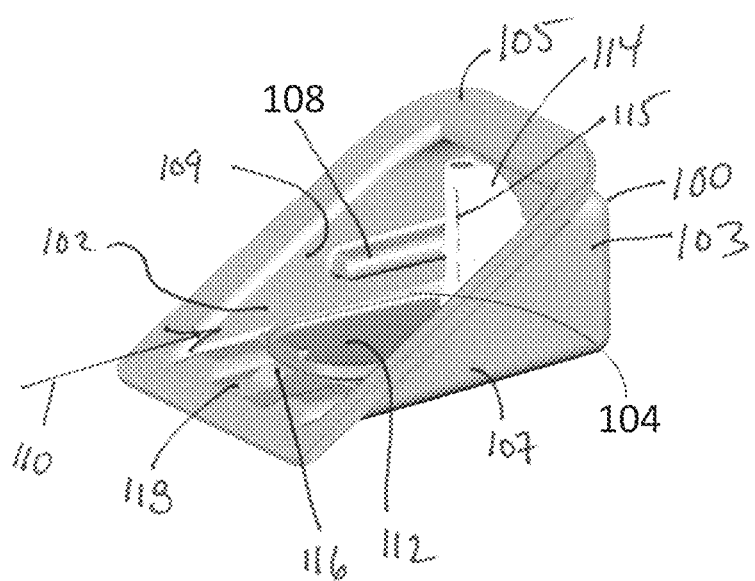

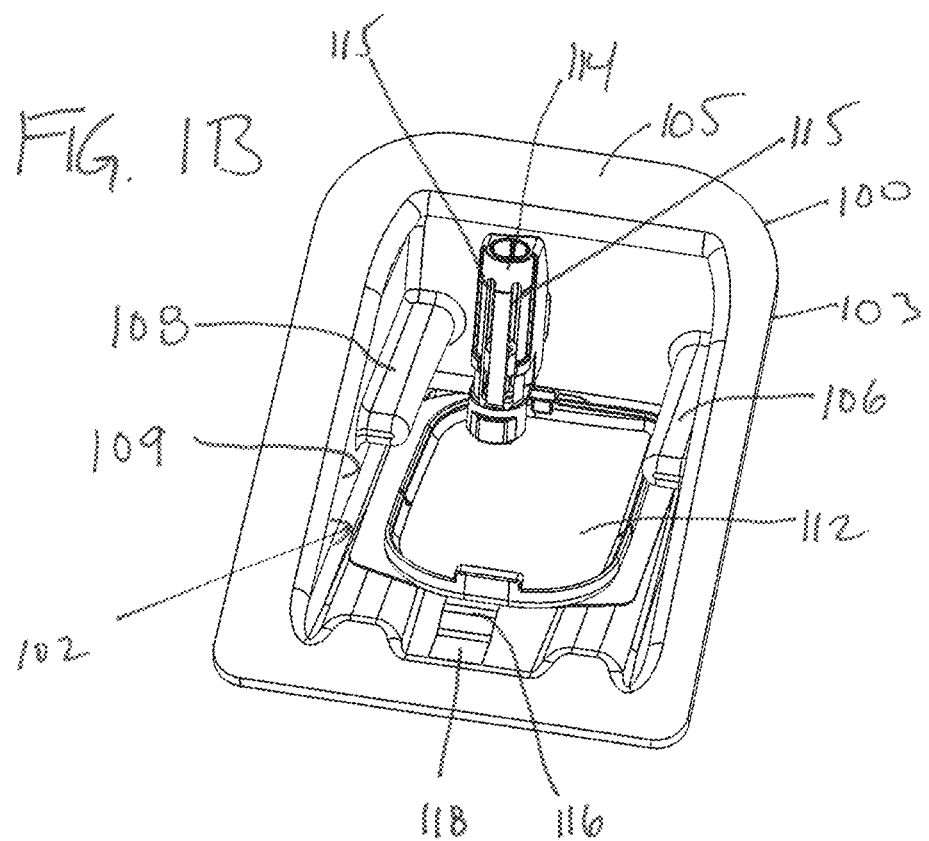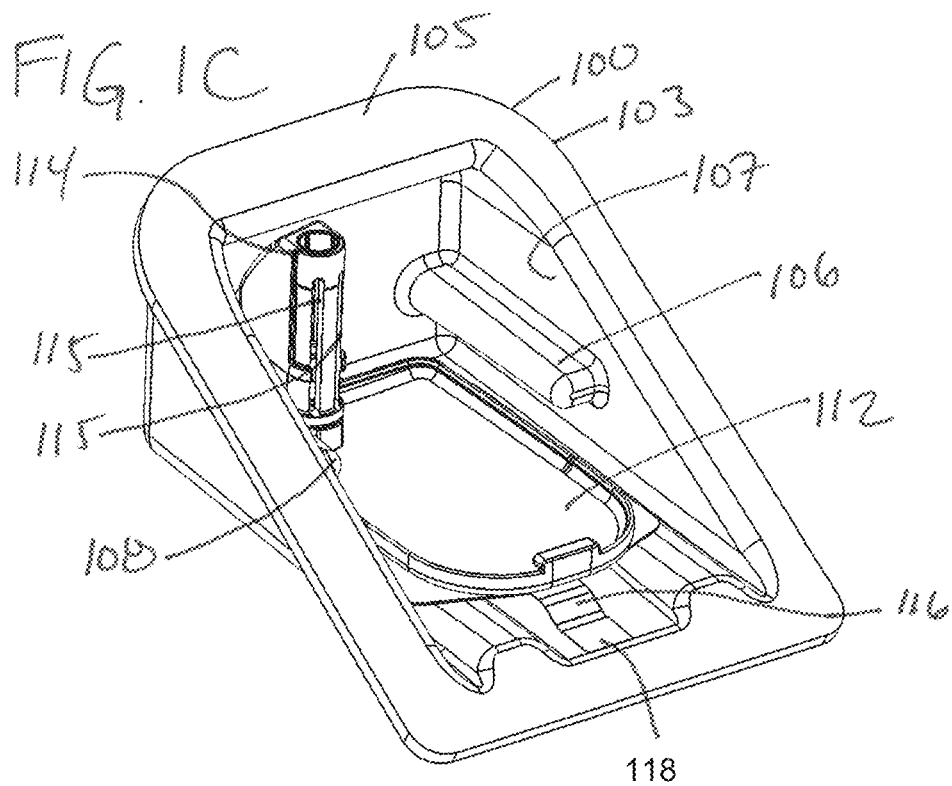

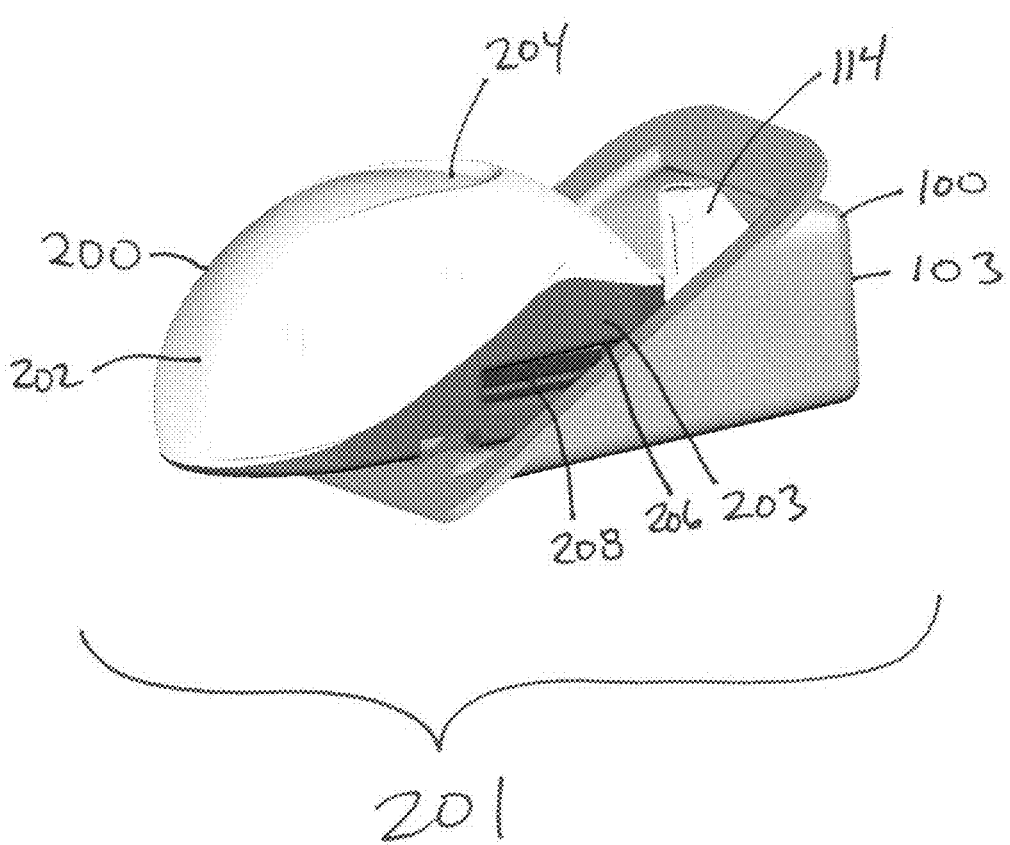

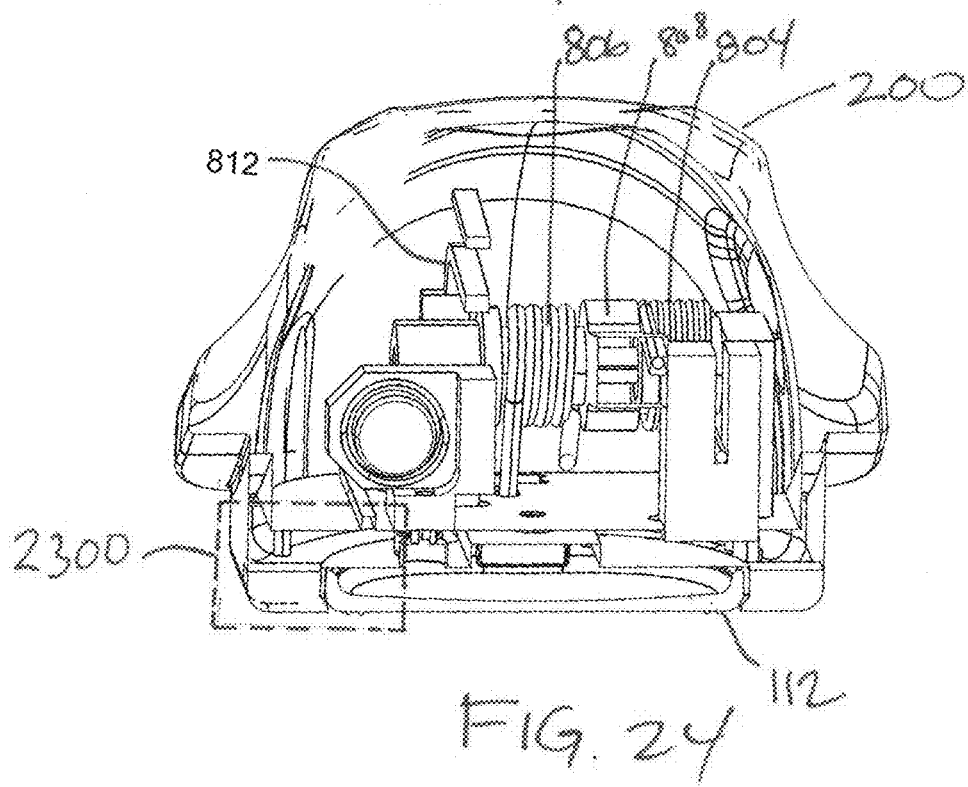
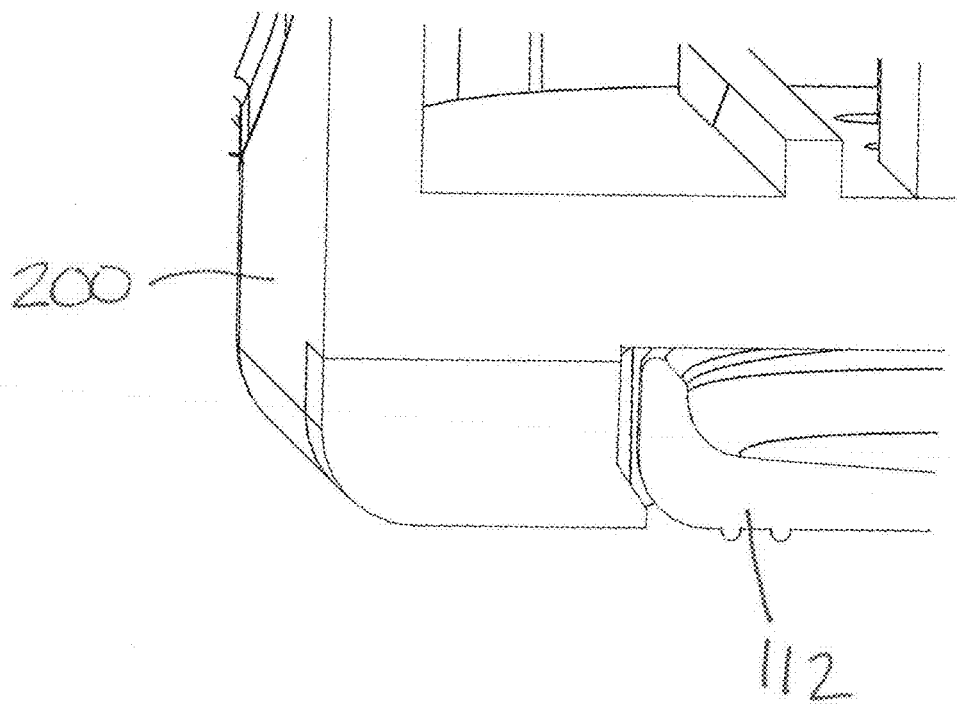

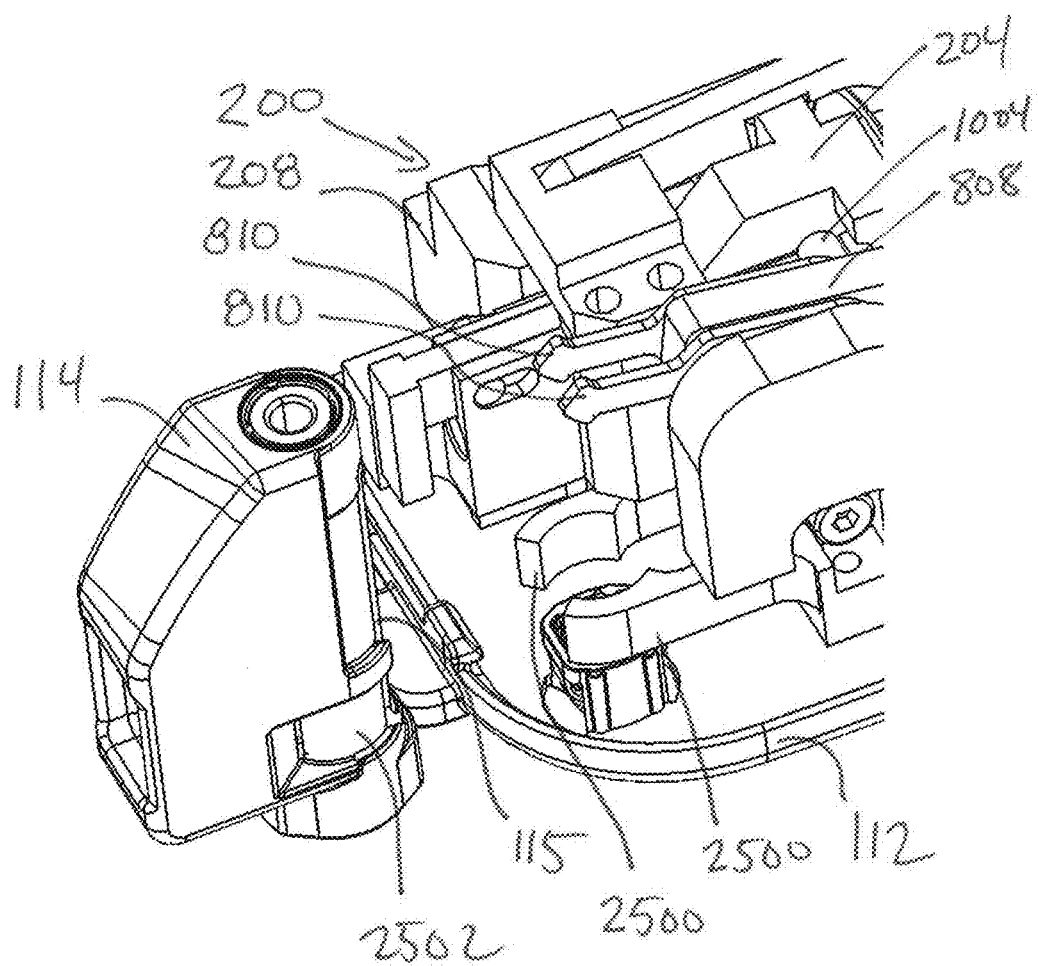

CARTRIDGE AND INSERTER FOR A MEDICAL SYSTEM

RELATED APPLICATIONS

This application is a continuation of PCT/EP2016/061860, filed May 25, 2016, which claims priority to EP 15169214.2, filed May 26, 2015, the entire disclosures of which are hereby incorporated herein by reference in their entireties.

BACKGROUND

This disclosure relates to inserters and disposables for inserting a subcutaneous element into a subject.

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated blood glucose levels that result from defects in the body's ability to produce and/or use insulin. There are three main types of diabetes. Type 1 diabetes may be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

Diabetes is managed primarily by controlling the level of glucose in the bloodstream. This level of blood glucose entering the bloodstream is dynamic and complex, and is affected by multiple factors including the amount and type of food consumed, and the amount of insulin (which mediates transport of glucose across cell membranes) in the blood. Variation of insulin in the bloodstream that controls the transport of glucose out of the bloodstream also complicates diabetes management. Blood glucose levels are also sensitive to diet and exercise, but also can be affected by sleep, stress, smoking, travel, illness, menses, and other psychological and lifestyle factors unique to individual patients. The dynamic nature of blood glucose and insulin and all other factors affecting blood glucose often require a person with diabetes to track and forecast blood glucose levels. Therefore, therapy in the form of insulin, oral medications, or both can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information such as blood glucose is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates, and proteins along with effects of exercise or other physiological states. The management of lifestyle factors such as body weight, diet, and exercise can significantly influence the type and effectiveness of therapy.

The use of a medical appliance that can monitor and/or provide insulin to the patient can be beneficial for maintaining proper glucose levels. The use of a medical appliance may involve mounting a pump or sensor assembly on the body and/or clothing and inserting one or more cannulas into the body. This, however, may be difficult for some patients. The loss of motor skills due to old age, diabetes, or the side effects of insulin itself may make it difficult for a patient to properly mount a pump and/or monitor and to properly insert a cannula or sensor into the body. It is therefore of great benefit to simplify the process using a medical appliance to make it less dependent upon the use of fine motor skills. Furthermore, it is of great benefit to provide a reusable inserter that requires only a few simple handling steps to insert the disposable parts like a cannula and/or a sensor.

WO 2007031126 A1 discloses an insertion head for medical or pharmaceutical applications, comprising: a base with a lower side which can be placed on organic tissue, an insertion device, movably received by the base, which can be inserted into the tissue, said insertion device being movable in relation to the base from a protected position in which a free end of the insertion device is recessed from the lower side of the base to an insertion position in which the free end projects beyond the lower side of a handle projecting from the base and comprising a first handle component and a second handle component, movable in relation to the base and the first handle component, and a coupling that translates a movement of the second handle component into a movement of the insertion device.

U.S. Pat. No. 7,879,010 discloses a device for inserting a cannula into tissue, including a cannula, a protective element which can accommodate said cannula, an operating element for moving the cannula out of the protective element, and a holder fixedly connected to the cannula.

U.S. Pat. No. 7,815,607 discloses an insertion device for an infusion set, the device including a retention means by which the infusion set can be temporarily held on the device and drive means including a pretensionable spring for providing drive energy for an insertion movement of the infusion set. The infusion set is secured by the retention means by clamping when the retention means is in an engage position and can then be moved, with simultaneous pretensioning of the spring, to an insertion movement starting position. The infusion set is already separated from the retention means at the start of the insertion movement. The infusion set moves through at least part of the insertion movement free of the retention means.

SUMMARY

This disclosure teaches a method of using a medical system, a cartridge, an inserter, and a medical system.

In one aspect, this disclosure provides for a method of using the medical system. The medical system comprises a cartridge and an inserter. In some examples, the inserter is configured to be re-usable rather than a single use diposable inserter.

The cartridge comprises a housing with an interior volume. The housing comprises a first guiding structure within the interior volume. The cartridge further comprises a cradle for mounting a medical appliance.

The cradle comprises a subcutaneous element. The subcutaneous element may for example be one or more cannulas and/or one or more sensors. The one or more sensors may for example include a glucose sensor, a lactate sensor, and an oxygen sensor.

The cradle is located within the interior volume. The cradle further comprises an insertion needle. The insertion needle is configured for being actuated to insert the subcutaneous element into the subject.

The inserter comprises a second guiding structure for mating with the first guiding structure. The first guiding structure and the second guiding structure are configured for guiding a portion of the inserter into the interior volume along a guiding path. The portion of the inserter is configured for removably attaching to the cradle when guided into the interior volume. The inserter further comprises an insertion mechanism (also referred to as an insertion assembly or insertion drive) for actuating the insertion needle to insert the subcutaneous element into the subject.

The method comprises the step of moving the portion of the inserter into the interior volume of the housing along the guiding path or in an insertion direction. Moving the portion of the inserter into the interior volume causes the cradle to attach to the portion of the inserter. The method further comprises the step of removing the portion of the inserter and the cradle from the interior volume.

In another embodiment, the cradle comprises an adhesive layer for attaching to an exterior surface of a subject.

In another embodiment the method further comprises the step of attaching the cradle to the exterior surface of the subject. The method further comprises the step of operating the insertion mechanism to actuate the insertion needle to insert the subcutaneous element into the subject. The method further comprises the step of removing the inserter from the cradle.

In another embodiment the insertion mechanism comprises a stored energy source, also referred to as a stored energy component, for driving the insertion needle into the subject and withdrawal of the insertion needle from the subject. The first guiding structure comprises a rigid element for engaging the stored energy component. The stored energy component is configured for being primed when pressed against the rigid element when the inserter is moved into the interior volume of the housing along the guiding path. The method further comprises priming the stored energy component during the insertion of the portion of the inserter into the interior volume of the housing along the guiding path. This embodiment may be beneficial because the needle is attached to the inserter at the same time that the stored energy component is primed or loaded with energy.

In another embodiment the cradle comprises a removable needle housing. The insertion needle has an extended position and a retracted position. The insertion needle is within the removable needle housing when in the retracted position. The method further comprises removing the removable needle housing from the cradle after removing the inserter from the cradle. This embodiment may be further beneficial because it provides for a means of disposing of a needle after the insertion has been performed. In some examples the removable needle housing may serve as a disposable sharps container that accompanies the needle.

In another aspect, this disclosure provides for a cartridge. The cartridge comprises a housing with an interior volume. The housing comprises a first guiding structure within the interior volume for guiding a second guiding structure of an inserter along a guiding path. The cartridge further comprises a cradle for mounting a medical appliance. The cradle comprises a subcutaneous element. The cradle is within the interior volume. The cradle further comprises an insertion needle. The insertion needle is configured for being actuated to insert the subcutaneous element into the subject.

In another embodiment, the cradle comprises an adhesive layer for attaching to an exterior surface of a subject.

In another embodiment the first guiding structure comprises a rigid element for engaging the stored energy component of an insertion mechanism of the inserter.

In another embodiment the cradle comprises a backing material layer covering the adhesive layer to prevent the adhesive layer from sticking to the interior volume. The housing has an entrance to the interior volume. A portion of the backing material closest to the entrance is attached to the housing. This may be beneficial because a portion of the backing material attached close to the entrance causes the backing material layer to automatically peel off of the adhesive layer as the cradle is removed.

In another embodiment the attachment of the backing material to the housing is configured to automatically peel the backing from the adhesive layer when the cradle is removed from the housing along the guiding path.

The portion of the backing material attached to the housing is configured to remain attached to the housing when the cradle is removed from the housing along the guiding path. This may be beneficial because it reduces the number of pieces that a user of the cartridge needs to dispose of.

In another embodiment the cradle comprises a removable needle housing. The insertion needle has an extended position and a retracted position. The insertion needle is within the removable needle housing when in the retracted position. The removable needle housing may provide a convenient way of disposing of the insertion needle safely as no sharps container is needed for disposal of the insertion needle.

In another embodiment the removable needle housing comprises at least one slot that is parallel to the insertion needle. The insertion needle comprises a mechanism attachment point for attaching to the insertion mechanism. The at least one slot provides clearance for a mechanism to actuate the insertion needle.

In another embodiment the housing is a blister pack. This may be beneficial because it provides an inexpensive and sterile packaging for the needle within the housing.

In some examples, the blister pack may be made of plastic and/or metal based materials. It may be vacuum formed or injection molded.

In another embodiment the housing has an opening to the interior volume.

In another embodiment the housing comprises a lid for sealing the opening. The lid may also be referred to as a lid seal or lidding seal. In some examples, the lid is a foil that provides a germ proof or sterile seal. In some examples the lid is attached to the housing via hot melt, thermos, ultrasonic or laser welding.

In another embodiment the lid is formed from any one of the following: aluminum foil, plastic, paper, and combinations thereof.

In another embodiment the interior volume is sterile.

In another embodiment the opening is planar.

In another embodiment the interior volume has a rectangular profile perpendicular to the guiding path. The opening is tilted with respect to the rectangular profile.

In some examples the housing has a pie shaped profile. A pie shaped profile is a profile that is similar in shape to a sector of a circle or is triangular in shape. The pie shape may have the advantage that it minimizes storage volume and simplifies the handling for the user.

In another embodiment the opening is tilted with respect to the rectangular profile between 20° and 60°.

In another embodiment the housing is at least partially formed by a thermal formed plastic.

In another embodiment the thermal formed plastic is any one of the following: polyvinyl chloride, polychlorotrifluoroethylene, cyclic olefin copolymers, and cyclic olefin polymers.

In another embodiment the first guiding structure is formed in a first sidewall of the interior volume.

In another embodiment the rigid structure is formed from a portion of the first sidewall.

In another embodiment the interior volume has as second sidewall opposing the first sidewall. The sidewall comprises a supplementary guiding structure.

In another embodiment the supplementary guiding structure is aligned with the guiding path.

In another embodiment the first guiding structure is aligned with the guiding path.

In another aspect, this disclosure provides for an inserter. The inserter comprises a second guiding structure for mating with the first guiding structure of a cartridge. The second guiding structure is configured for guiding a portion of the inserter into the interior volume along a guiding path defined by the first guiding structure. The cartridge comprises a cradle. The portion of the inserter is configured for removably attaching to the cradle when guided into the interior volume. The cradle comprises an insertion needle. The inserter further comprises an insertion mechanism for actuating the insertion needle to insert the subcutaneous element into the subject.

In another embodiment the insertion mechanism comprises an energy storage component for driving the insertion needle into the subject and out of the subject. The first guiding structure comprises a rigid element for engaging the energy storage component. The energy storage component is configured for being primed when pressed against the rigid element when the inserter is moved into the interior volume of the housing along the guiding path.

In another embodiment the inserter comprises a cover. The second guiding structure is a first groove in the cover. The insertion mechanism comprises a sliding element for sliding within the first groove. The sliding element is configured for priming the energy storage component when moved along the first groove.

In another embodiment the inserter further comprises an additional guiding structure. The additional guiding structure is a second groove in the cover. The additional guiding structure is aligned with the guiding path.

In another embodiment the additional guiding structure mates with the supplementary guiding structure.

In another embodiment the insertion mechanism comprises a button for activating the insertion mechanism when the stored energy component is primed.

In another embodiment the insertion mechanism comprises a safety element which may also be referred to as a safety or safety mechanism. The safety element extends through the adhesive layer when the stored energy component is primed. T he inserter has a mounting surface. The mounting surface is flush with the adhesive layer. The safety element is configured for being depressed flush with the mounting surface when the stored energy component is primed. The insertion mechanism is locked unless the safety element is depressed flush with the mounting surface. This may be beneficial because it may prevent the insertion mechanism from being activated when the inserter is not attached to a subject.

In another aspect, this disclosure provides for a medical system. The medical system comprises a cartridge according to an embodiment. The medical system further comprises an inserter according to an embodiment.

In another embodiment the medical system comprises a medical appliance for mounting into the cradle.

In another embodiment the subcutaneous element comprises at least one cannula. The medical appliance comprises a pumping system. The pumping system comprises any one of the following: an insulin pump for pumping insulin through the at least one cannula, a glucagon pump for pumping glucagon through the at least one cannula, and combinations thereof.

In another embodiment the subcutaneous element comprises a glucose sensor. The medical appliance comprises a continuous glucose monitor.

In another embodiment a cradle with one or two cannulas and/or a sensor could be present in a single cradle. In one example the inserter could insert two cannulas at the same time. In another example a cannula and one or more sensors could be inserted at the same time. In another example two cannulas and one or more sensors could be inserted at the same time. In these examples, the inserter mechanism could actuate multiple insertion needles. In other examples a single needle is used to insert multiple subcutaneous elements.

In other words, a single cradle might have multiple subcutaneous elements that can be inserted by a single inserter.

In another embodiment the portion of the inserter is configured for forming a snap-fit to removably attach to the cradle when guided into the interior volume.

It is understood that one or more of the aforementioned embodiments disclosed herein may be combined as long as the combined embodiments are not mutually exclusive.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1A illustrates an example of a cartridge;

FIG. 1B further illustrates the example of FIG. 1A;

FIG. 1C further illustrates the example of FIG. 1A;

FIG. 2 illustrates an example of a medical system comprising an inserter and the cartridge of FIG. 1;

FIG. 23 shows a cross sectional view of an inserter that is mounted on a cradle;

FIG. 24 shows an enlarged region of FIG. 23;

FIG. 25 illustrates an example of how a removable needle assembly interfaces with an inserter;

DESCRIPTION

Figure 3:
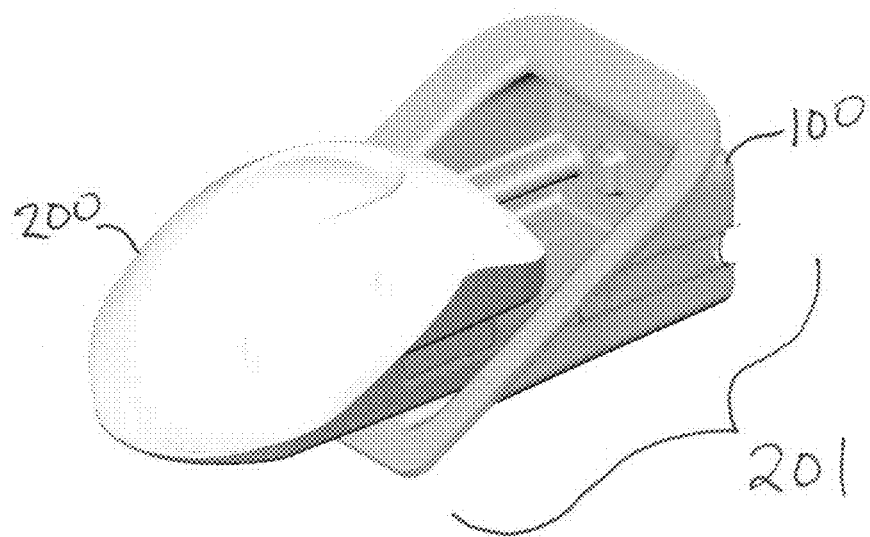
FIG. 3 shows the medical system of FIG. 2 after the inserter has been inserted into and partially removed from the cartridge.

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Like numbered elements in these figures are either equivalent elements or perform the same function. Elements which have been discussed previously will not necessarily be discussed in later figures if the function is equivalent.

FIGS. 1A, 1B, and 1C are three different views which illustrate an example of a cartridge 100. The cartridge 100 has an opening 102 in a housing 103. The opening 102 provides access to an interior volume 104 of the cartridge 100. There is a sealing surface surface 105 which can be used to attach a lid or a lidding seal such as a metal and/or plastic foil.

There is a first guiding structure 106 and a supplementary guiding structure 108. The first guiding structure is shown as being formed as part of a first side wall 107. The supplementary guiding structure 108 is shown as being formed as part of a second side wall 109. In this example both guiding structures 106, 108 are identically formed. They are both ridges of solid material which are aligned with a guiding path 110. The figures show how the supplementary guiding structure 108 extends into the interior volume 104. In this example the cartridge 100 is formed from a blister pack or thermoformed plastic. The first guiding structure 106 extends into the interior volume 104 in the same way that the supplementary guiding structure 108 does.

Within the interior volume 104 there is a cradle 112. The cradle has attached to it a movable needle housing 114 that houses a needle. There is a slot or slots 115 which a mechanism can use to enter and actuate the needle within the removable needle housing 114. On the underside of the cradle 112, there is a backing material 116 which protects an adhesive layer. The backing material 116 is attached to the interior volume 104 at an attachment point 118. In this case it is the portion of the backing material 116 that is closest to the opening 102. As the cradle 112 is removed from the housing 103 the backing material 116 is peeled off from the cradle 112, exposing the adhesive layer.

FIG. 2 shows an example of an inserter 200 being inserted into the cartridge 100 along the guiding path 110. The inserter 200 and the cartridge 100 are part of a medical system 201. The inserter 200 can be seen as having a cover 202. There is a button 204 on the inserter 200 to fire an insertion mechanism which is contained within the cover 202. In FIG. 2 there can be seen a second guiding structure 206 which is formed as a first groove in the cover 202. This second guiding structure 206 mates with the first guiding structure 106. Within the second guiding structure 206 is a sliding element or sliding member 208 which is used to charge or prime an energy storage element within the inserter 200. A portion 203 of the inserter 200 is inserted into the cartridge 100. As this is done, the sliding element 208 pushes against the first guiding structure 106 which is a rigid element. This pushes the sliding element 208 back and primes the insertion mechanism. On the far side of the cover 202 there is also an additional guiding structure which mates with the supplementary guiding structure 108. There is also a groove in the cover 202 that is used to help align and make the inserter 200 better follow the guiding path 110.

FIG. 2 shows the inserter 200 being inserted into the cartridge 100. The cradle 112 including the removable needle housing 114 will snap-fit into the inserter 200. As shown in FIG. 3, as the inserter 200 is withdrawn in the opposite direction to the guiding path 110 the cradle 112 is automatically removed. The backing material 116 is also automatically peeled off of the adhesive layer on the underside of the cradle 112.

Figure 4:
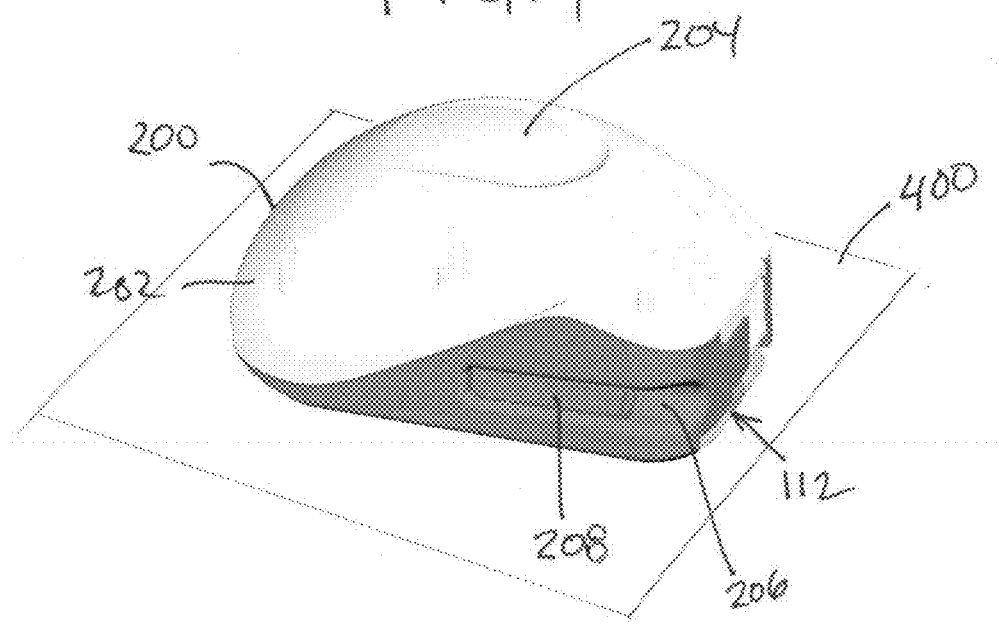
FIG. 4 shows the inserter of FIG. 2 after it has been removed from the cartridge.

FIG. 4 shows the inserter 200 after it has been completely removed from the cartridge 100. The sliding element 208 is no longer visible within the groove that forms the second guiding structure 206. It has been depressed into the energy storage component and is now hidden by the cover 202. The cradle 112 is on the underside of the inserter 200. The cartridge 200 shown in FIG. 4 could be attached to a subject by simply placing the inserter 200 on the surface or skin of a subject. Not shown in FIG. 4 is a safety element which is only engaged when the inserter 200 is placed on a surface. The square box 400 is representative of the surface 400 of the subject, which the inserter 200 is being placed on he square box 400 may also represent a surface of the inserter for mounting on the subject.

Figure 5:
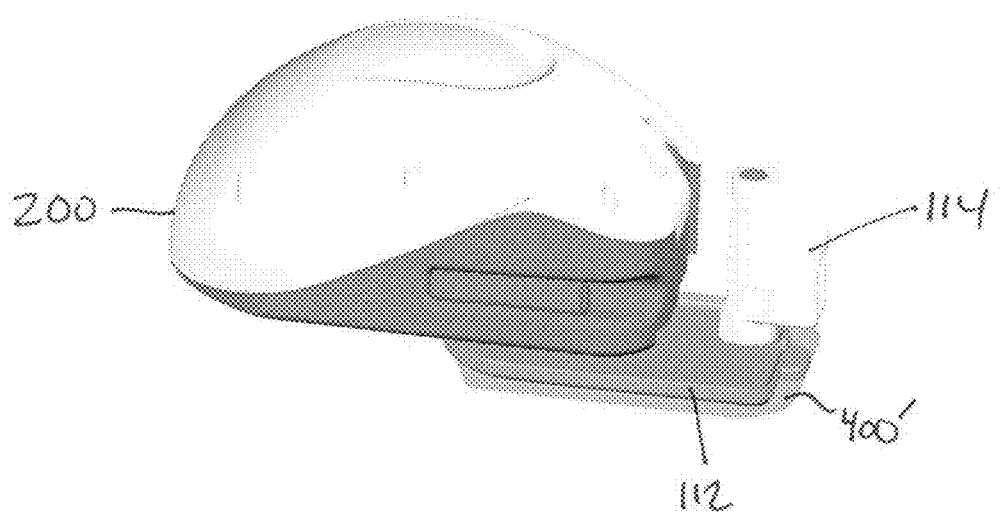
FIG. 5 shows the inserter of FIG. 2 as it is being removed from a cradle.

FIG. 5 shows the inserter 200 being removed from the cradle 112. The insertion mechanism has been actuated and the inserter 200 is then able to be easily slid apart from the cradle 112. The cradle 112 is adhered to an adhesive layer 400' which again adheres to the surface 400 of the subject.

Figure 6:
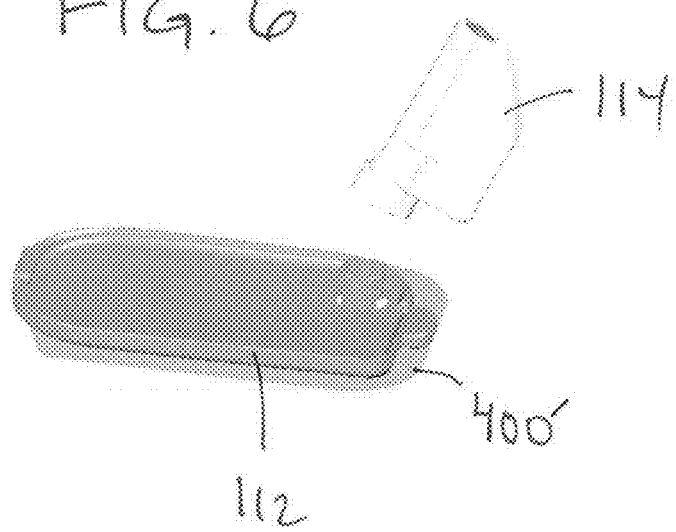
FIG. 6 shows a removable needle housing being removed from the cradle of FIG. 5.

FIG. 6 shows the removable needle housing 114 being removed from the cradle 112. The needle is within the removable needle housing 114. The removable needle housing 114 functions as a sharps container and the removable needle housing 114 can simply be thrown away.

Figure 7:
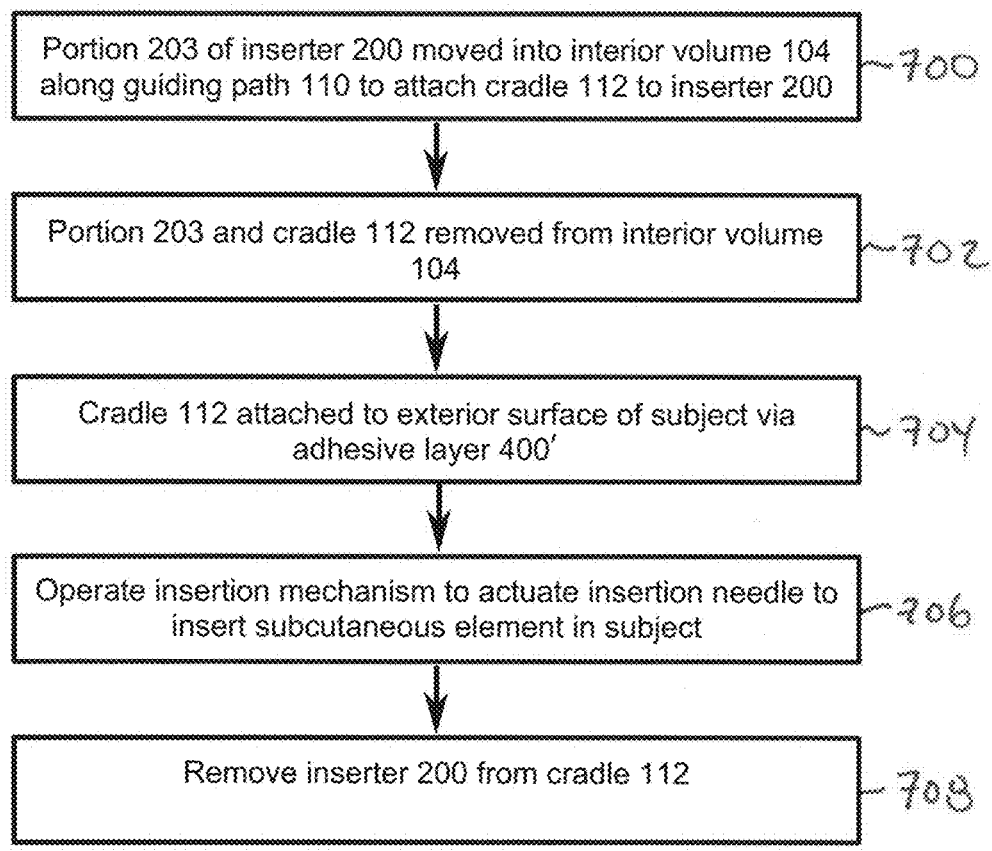
FIG. 7 illustrates a method of operating a medical system as is shown in FIGS. 1 through 6.

FIG. 7 shows a flowchart which illustrates a method of operating the medical system 201 shown in FIGS. 1-6. First in step 700 a portion 203 of the inserter 200 is moved into the interior volume 104 along the guiding path 110. After the inserter has been moved along the guiding path 110, the cradle 112 attaches to the inserter 200. Next in step 702, the portion 203 of the inserter 200 and the cradle 112 are removed from the interior volume 104. Next in step 704, the cradle 112 is attached to an exterior surface of a subject via the adhesive layer 400'. Next in step 706 the insertion mechanism is operated to actuate the insertion needle to insert a subcutaneous element into the subject. Finally in step 708, as is shown in FIG. 5, the inserter 200 is removed from the cradle 112.

Figure 8:
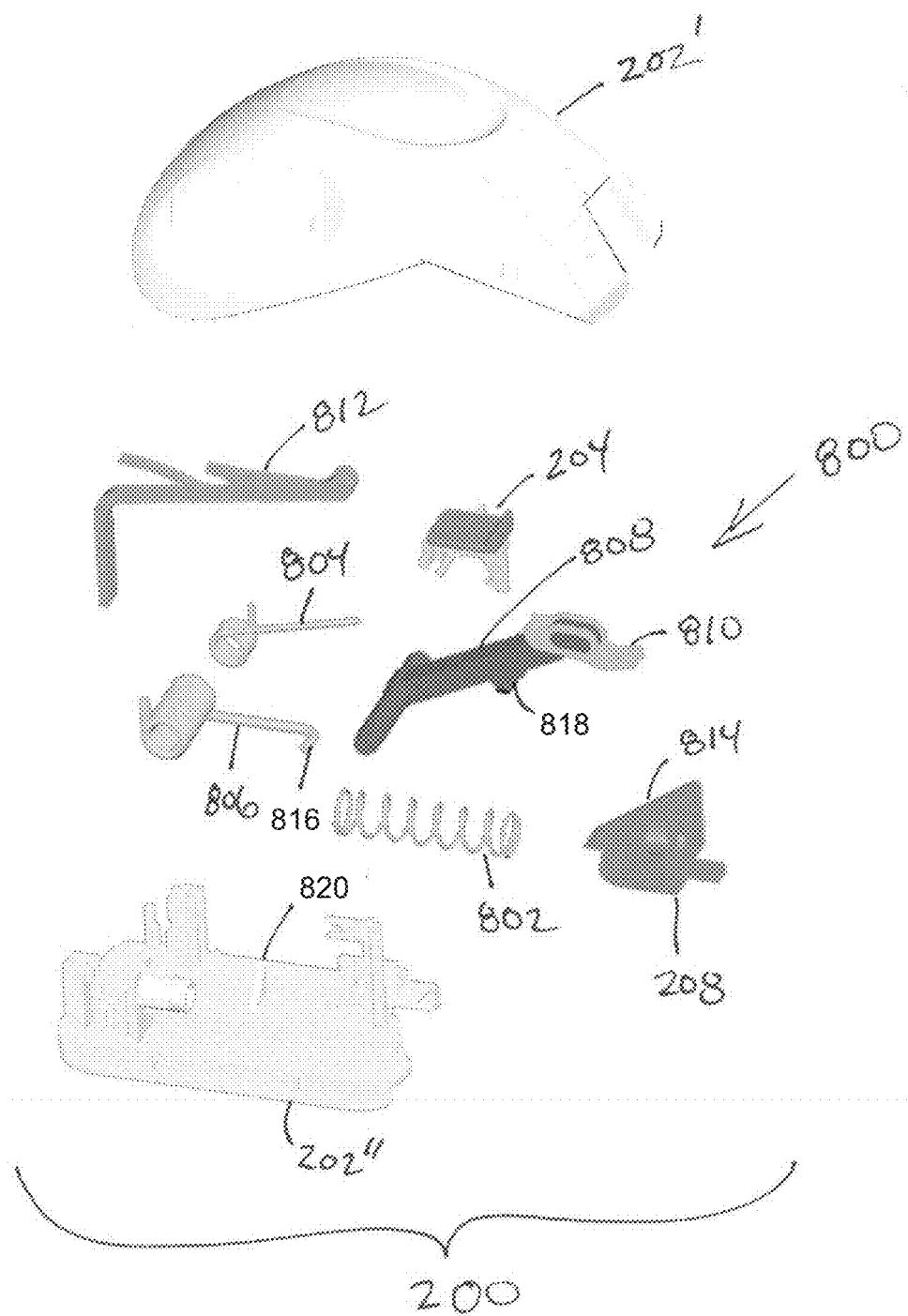
FIG. 8 shows an exploded view of an inserter.

FIG. 8 shows an exploded view of some components of the inserter 200. The cover 202 is comprised of a top cover 202' and a bottom cover 202". The bottom cover 202" also comprises some fixed elements of the insertion mechanism 800. In the components there can be seen the sliding element 208 which is used to prime the insertion mechanism 800. When the sliding element 208 is depressed it charges, loads, or primes a drive spring 806 or a stored energy component 806. The spring 806 is used to drive a drive arm 808 which forces a needle driver 810 in a downward motion. The needle driver 810 is able to go through the slots 115 of the disposable needle enclosure 114. After the drive arm 808 has been depressed, the retraction spring 804 withdraws the drive arm 808 back up again to remove the needle from the subject. The spring 806 is stronger than the retraction spring 804. As the drive spring 806 drives the needle driver 810 towards the subject it also applies force to and charges the retraction spring 804. The drive spring 806 is then released from the mechanism and the spring 804 is able to return the drive arm 808 and the needle drive 810 to its original starting position. The component 204 is a button which is actuated through the top cover 202'. The component 812 is a safety element which prevents activation of the insertion mechanism 800 unless the bottom cover 202" is placed on a surface such as a subject.

Figure 9:
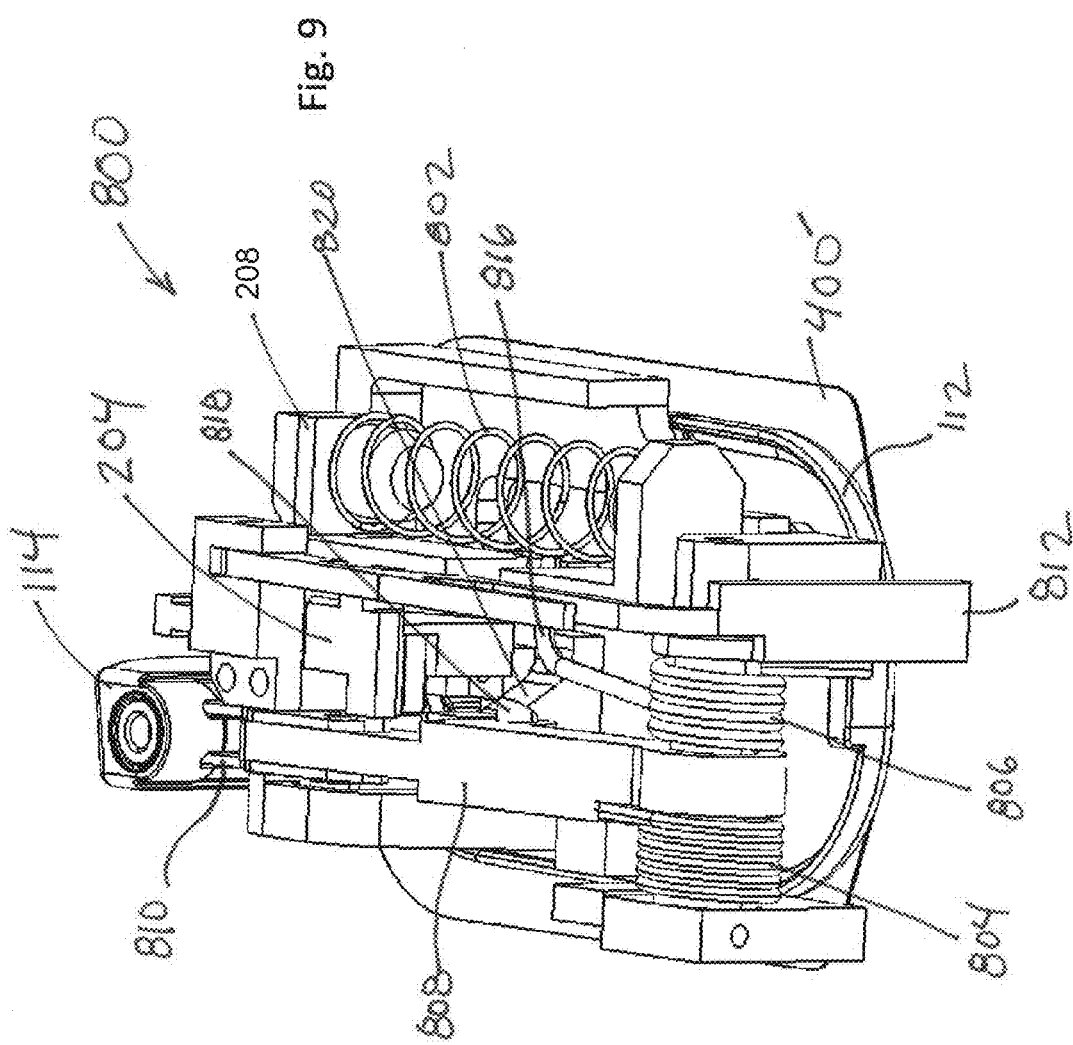
FIG. 9 shows an assembly drawing of the inserter of FIG. 8.

FIG. 9 shows a top view of the assembled insertion mechanism 800 of FIG. 8. The sliding element 208 has a sloped surface 14. This is used to engage an end point 816 of the driver spring 806. As the sliding element 208 is moved back the sloped surface 814 lifts the end point 816 and deposits it on a connection point 818 of the drive arm 808. When the drive arm 808 reaches a fully depressed position the end point 816 is forced off of the connection point 818 by a release element 820. In FIG. 8, it can be seen that in the bottom cover 202" there are a number of structures. The sloped component labeled 820 is the release element. The release element disengages the end point 816 from the connection point 818 when the drive arm 808 has been fully depressed. After the end point 816 has been disengaged from the connection point 818 the retraction spring 804 is then able to lift the drive arm 808 back into its original position.

Figure 10:
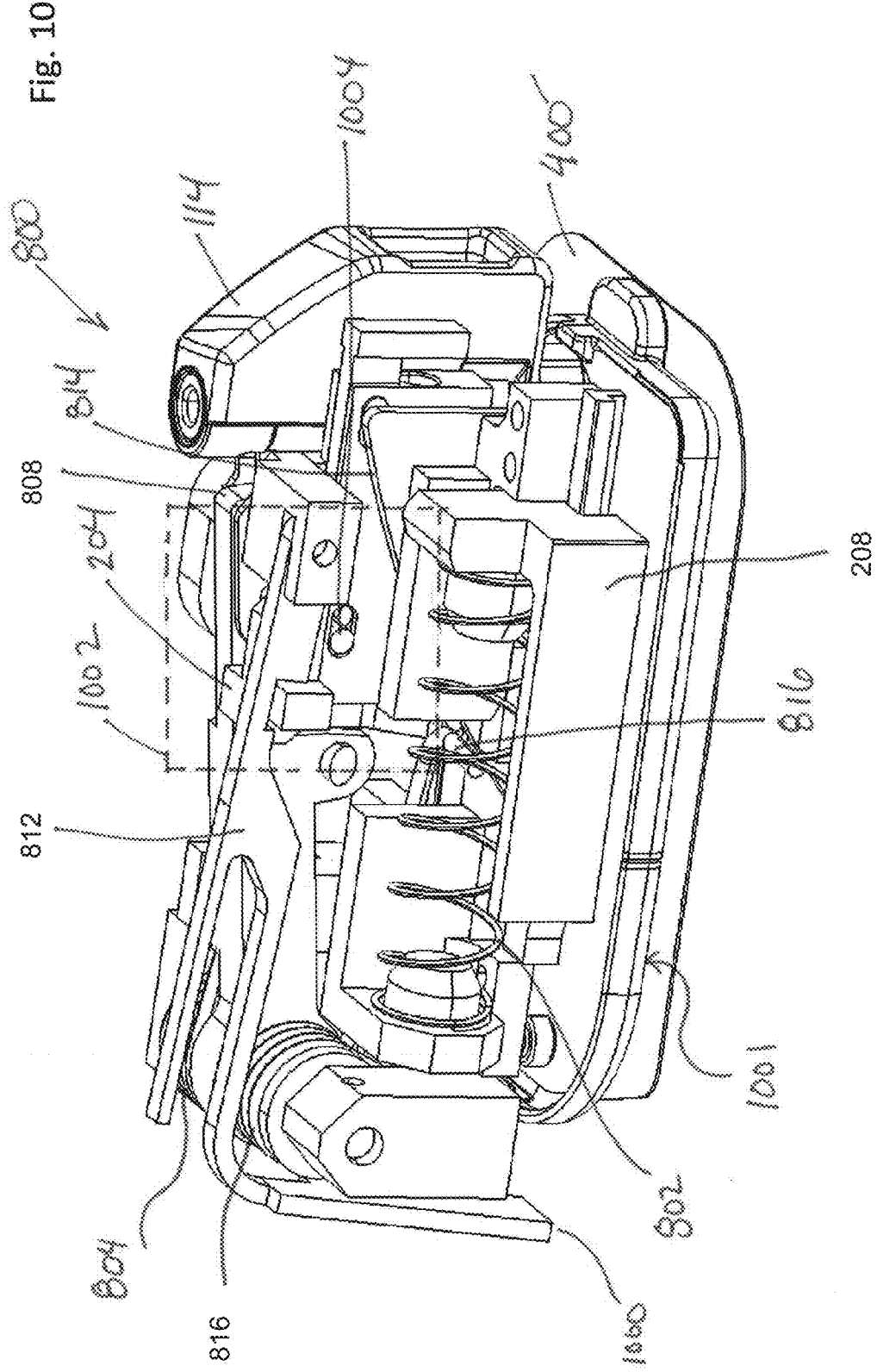
FIG. 10 shows a further assembly drawing of the inserter of FIG. 8.
Figure 11:
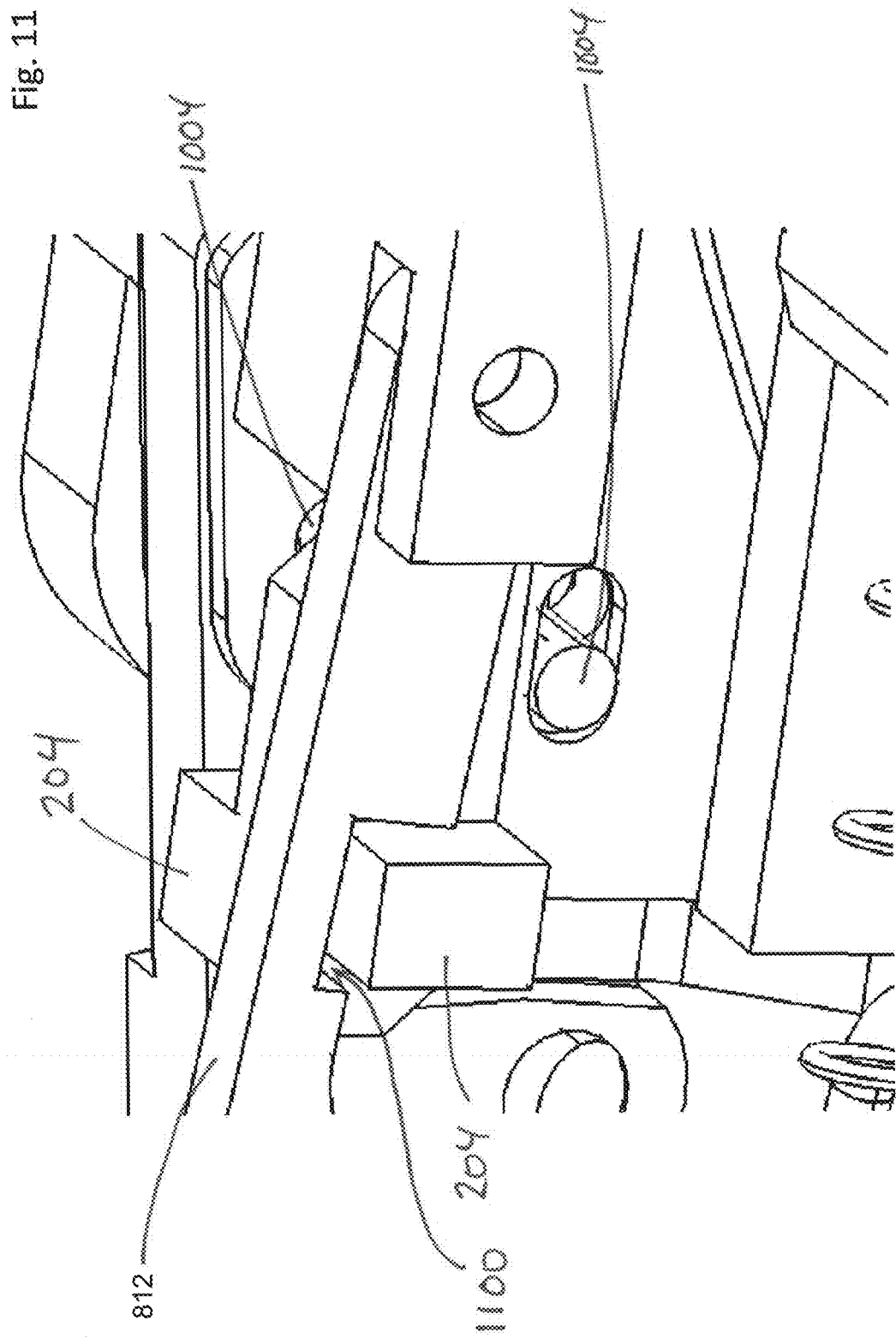
FIG. 11 shows a further assembly drawing of the inserter of FIG. 8.

FIG. 10 shows a perspective side view of the assembly drawing in FIG. 9. In particular in FIG. 10 it can be seen how the sloped surface 814 engages the end point 816. FIG. 10 also is useful for illustrating the function of the safety element 812 (also referred to as a safety). Unless the safety element 812 is properly engaged the switch or button 204 is not able to function. At the end point of the safety element 812 is a sensing point 1000. When the sensing point 1000 touches a surface such as the surface of the subject, it causes the sensing point to become flush with a mounting surface 1001 and the entire safety element 812 lifts up. The dashed region labeled 1002 is shown in an expanded view in FIG. 11. The safety element 812 has a notched region 1100 which locks the button 204 in place. When the safety element 812 is free and the sensing point 1000 is not touching anything the notched region 1100 falls into place and locks the position of the button 204. When the sensing point 1000 is placed on a surface it lifts the safety element 812 and the button 204 is free to move. The mechanism may then be activated. In FIGS. 9, 10 and 11 the insertion mechanism 800 has not yet been primed.

FIGS. 10 and 11 further show a release pin 1004. The release pin 1004 extends through the arm 808 and is supported by the button 204. When the button 204 is depressed the arm 808 is able to be actuated.

Figure 12:
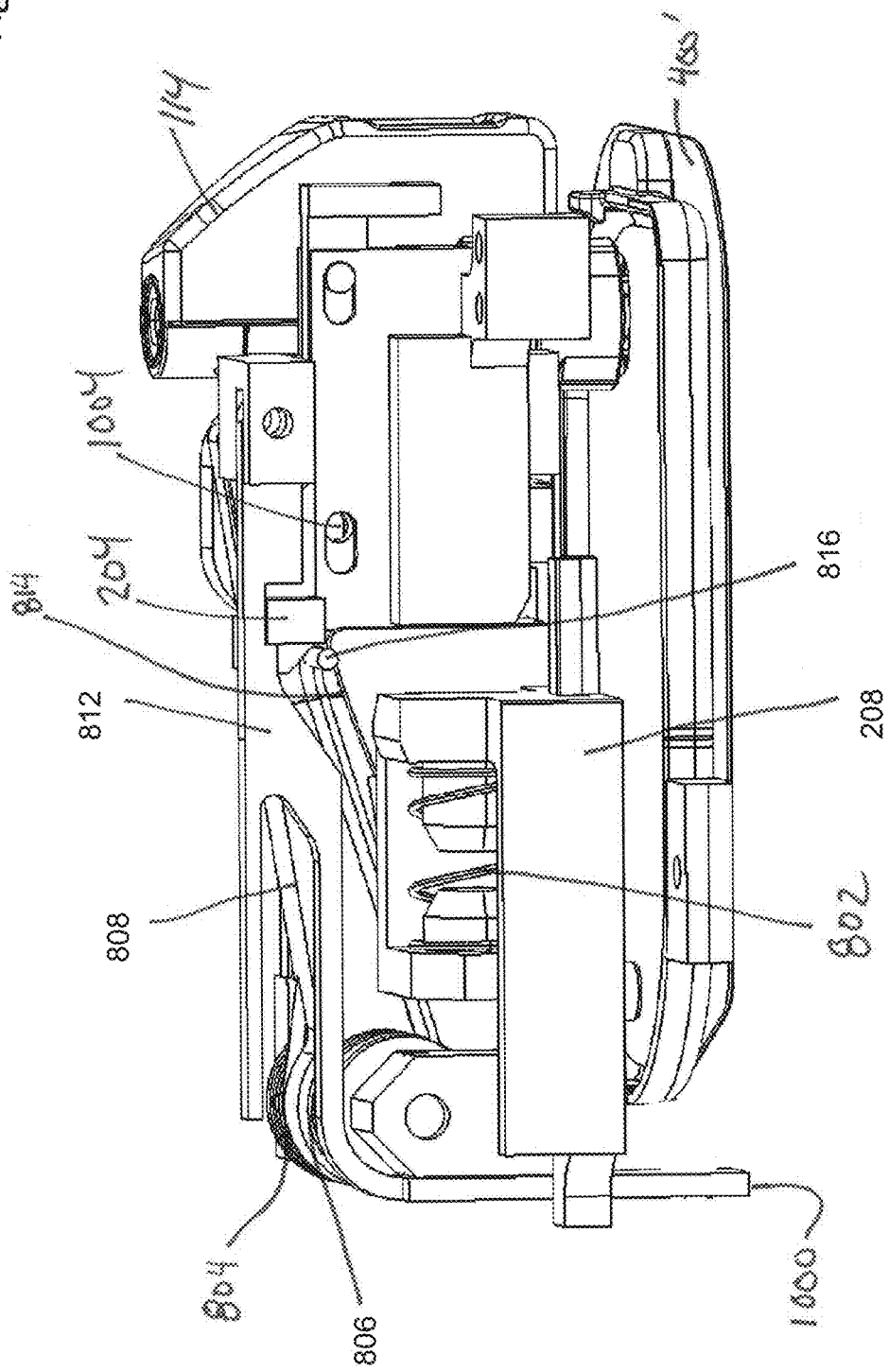
FIG. 12 shows a further assembly drawing of the inserter of FIG. 8.

FIG. 12 shows a side view of the insertion mechanism 800 before it has been primed. The sliding element 208 has been pushed back by the first guiding structure 106. The end point 816 has been lifted by the sloped edge 814 above the connection point 818 of the drive arm 808. It can be seen that the button 204 is holding the arm 808 of the spring above the connection point 818. When the button 204 is depressed the release pin 1004 no longer holds the drive arm 808 such that the arm 808 can move downwards.

Figure 13:
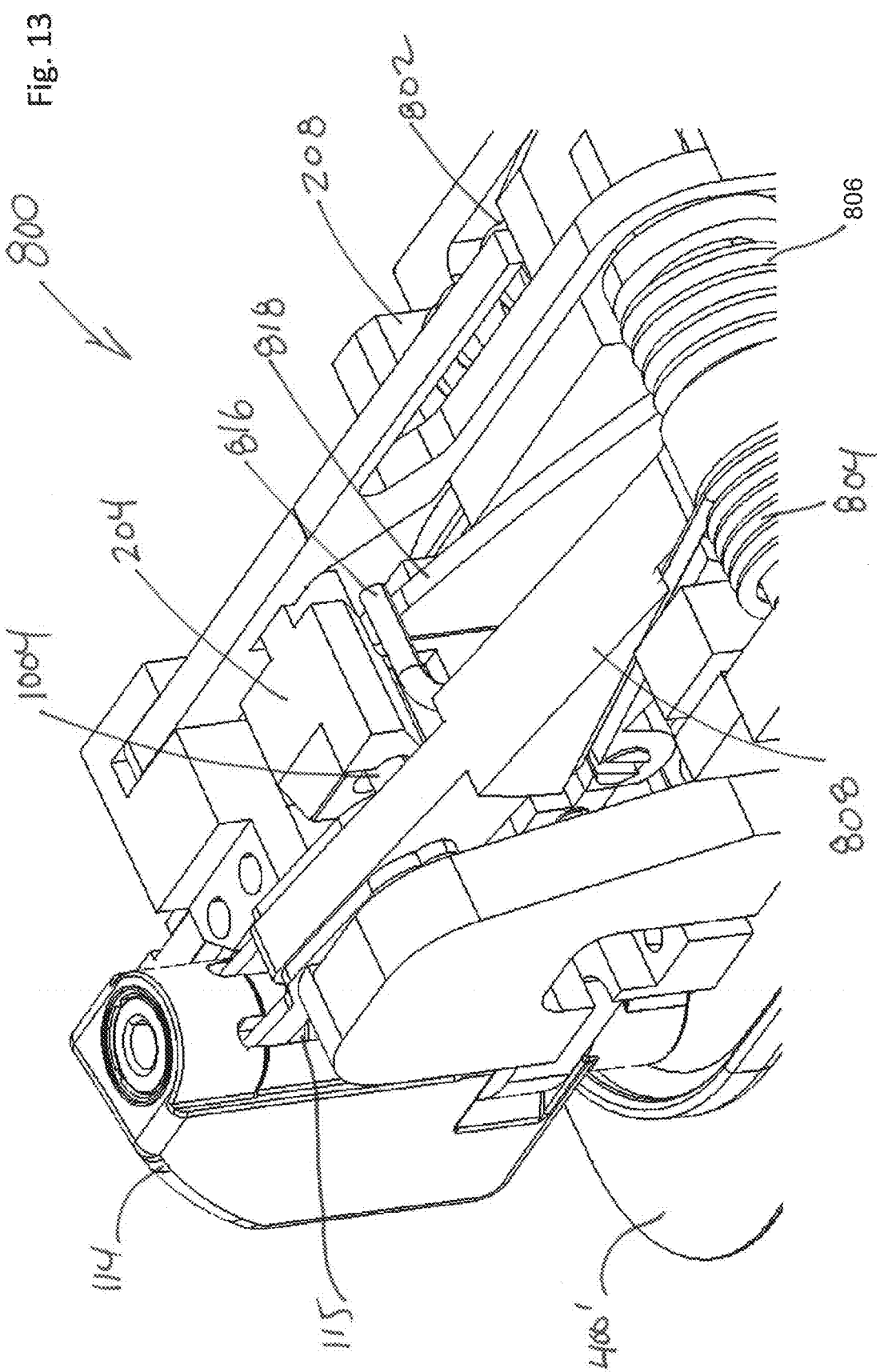
FIG. 13 shows a further assembly drawing of the inserter of FIG. 8.

FIG. 13 shows the same view of the insertion mechanism 800 of FIG. 12 but at a slightly different angle and position. In FIG. 13 it can be seen how the release button 204 holds the drive arm 808 in an upper position. When the button 204 is depressed the drive arm is no longer supported and the drive spring or stored energy component 806 is able to drive and actuate the drive arm 808.

Figure 14:
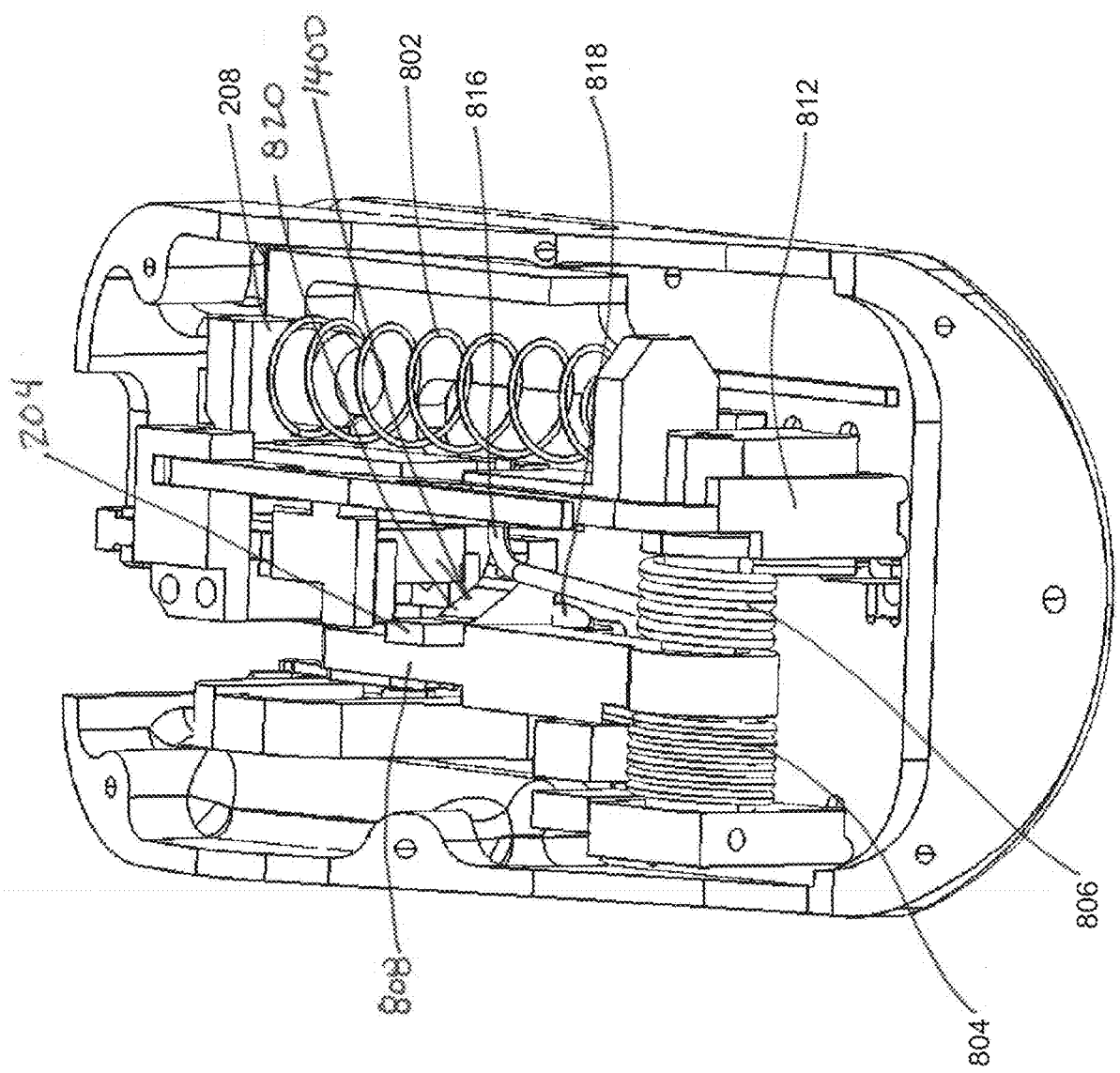
FIG. 14 shows a further assembly drawing of the inserter of FIG. 8.

FIG. 14 shows how the end point 816 of the drive spring 806 is disengaged from the connection point 818 of the drive arm 808. As the drive arm 808 is depressed the end point 816 of the drive spring 806 comes in contact with a curved surface 1400 of the release element 820. As the drive arm 808 reaches its fully depressed position the curved surface 1400 physically pushes the end point away and off of the connection point 818. At this point the drive spring 806 is no longer engaged and the retraction spring 804 is able to drive the drive arm 808 back into its original position.

Figure 15:
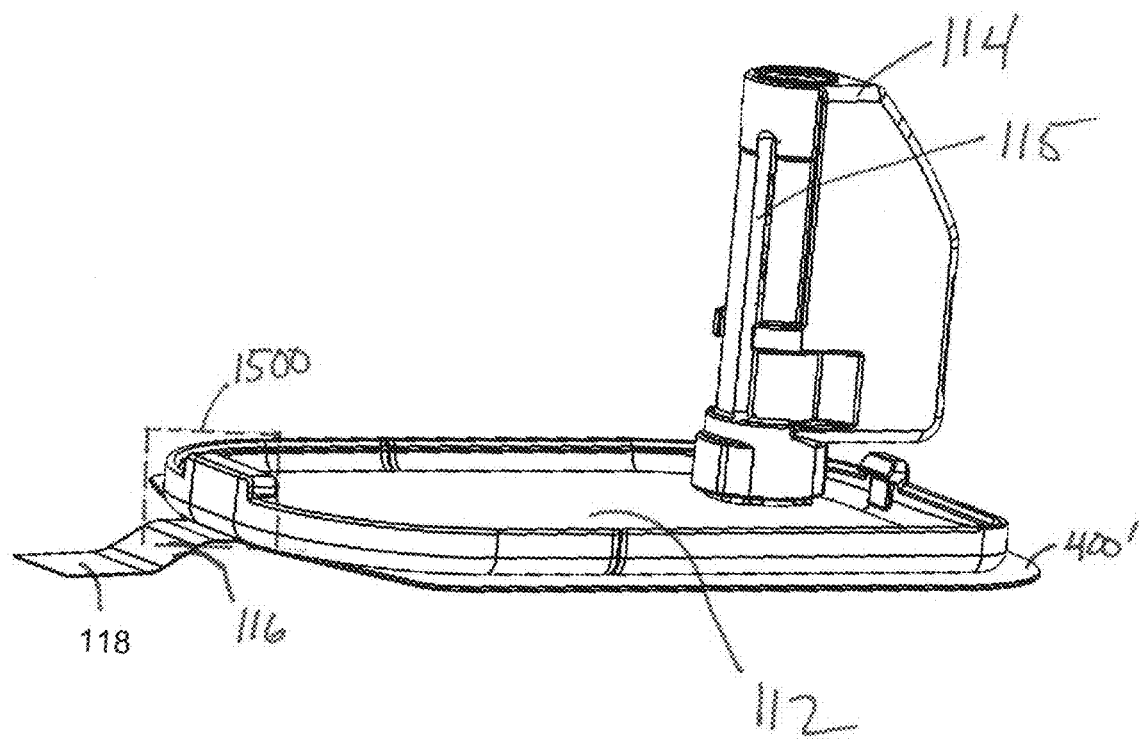
FIG. 15 shows an example of a cradle with a removable needle housing attached.
Figure 16:
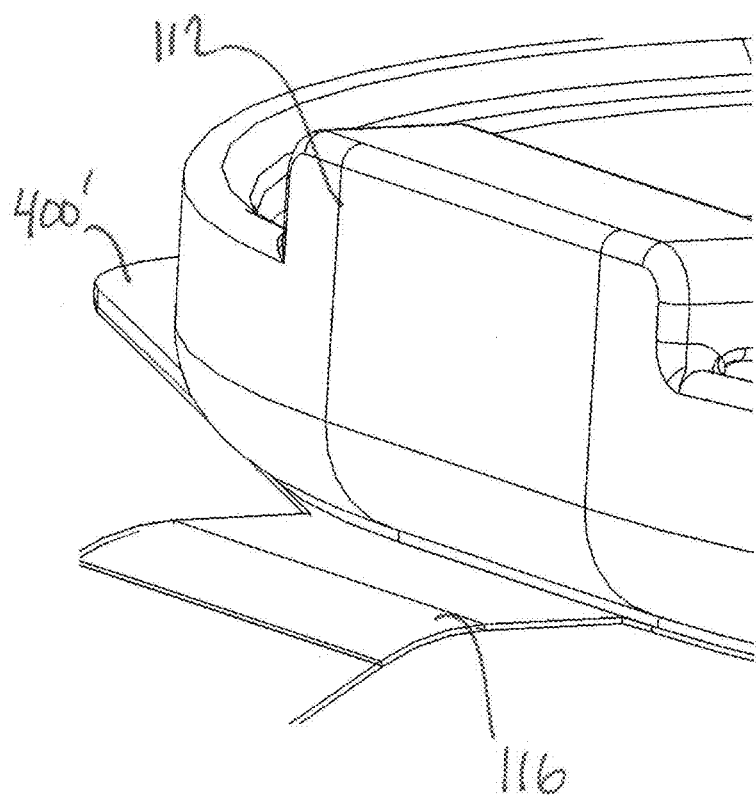
FIG. 16 shows an enlarged region of FIG. 15.

FIG. 15 shows an example of a cradle 112 with a removable needle housing attached. The box labeled 1500 shows a zoomed region which is shown in greater detail in FIG. 16. FIG. 16 shows how the adhesive layer 400' is attached to the cradle 112. The backing material 116 is shown as being attached to the adhesive layer 400'.

Figure 17:
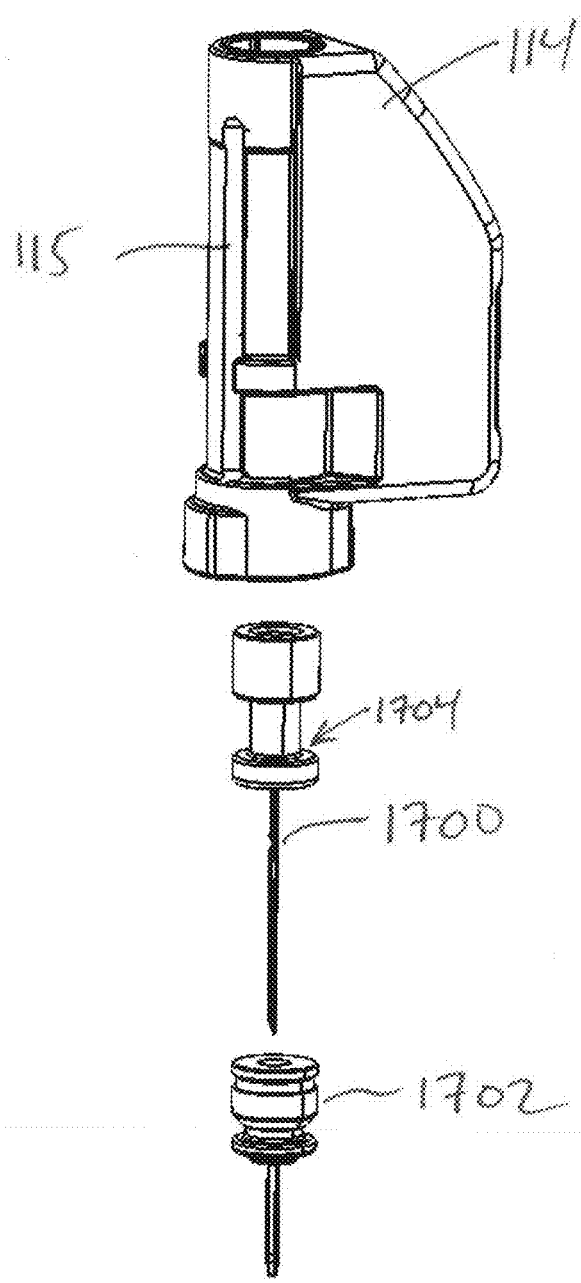
FIG. 17 shows an assembly drawing of a removable needle housing.

FIG. 17 shows an assembly drawing of the removable needle housing 114. The removable needle housing comprises an insertion needle 1700 and a cannula 1702. The cannula 1702 could be replaced by additional or different subcutaneous elements such as a sensor and/or additional cannulas. The insertion needle 1700 has a mechanism attachment point 1704 for attaching to an insertion mechanism. A portion of a mechanism may be inserted through the slot 115 and may be used to press against the mechanism attachment point 1704 to actuate the needle.

Figure 18:
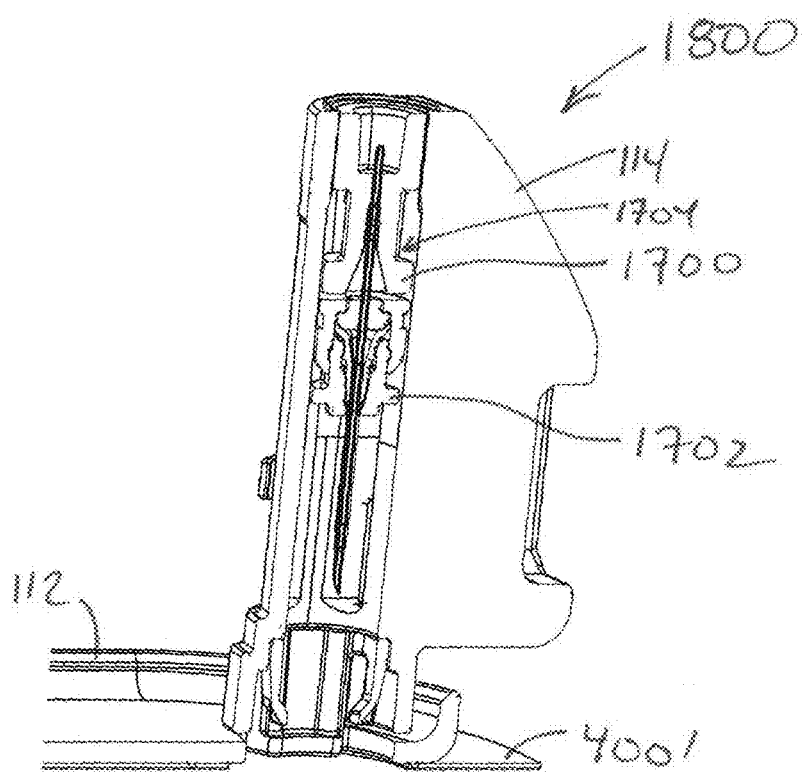
FIG. 18 shows a cross sectional view of the removable needle housing FIG. 17.

FIG. 18 shows a cross sectional view of the removable needle housing 114 of FIG. 17. In this cross sectional view, the needle is shown before being inserted into a subject. In FIG. 18, the insertion needle is in the retracted position 1800.

Figure 19:
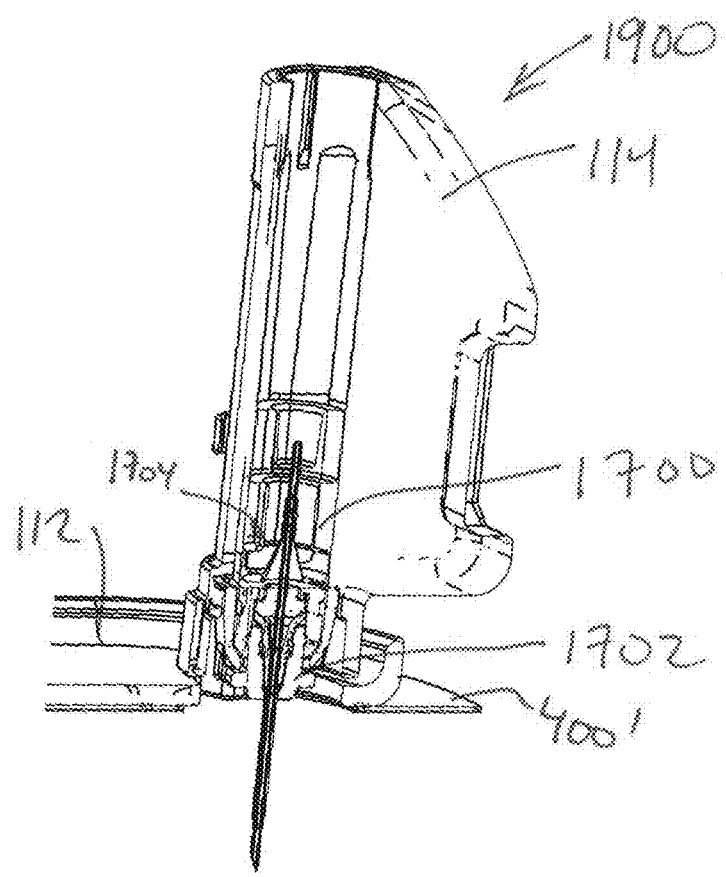
FIG. 19 shows a further cross sectional view of the removable needle housing of FIG. 17.

FIG. 19 shows a further cross sectional view of the removable needle housing 114 of FIG. 17. In this FIG., the insertion needle 1700 has been driven into a subject. When the insertion needle 1700 is withdrawn, the cannula 1702 will be left within the subject. In FIG. 19 the insertion needle is shown in the extended position 1900.

Figure 20:
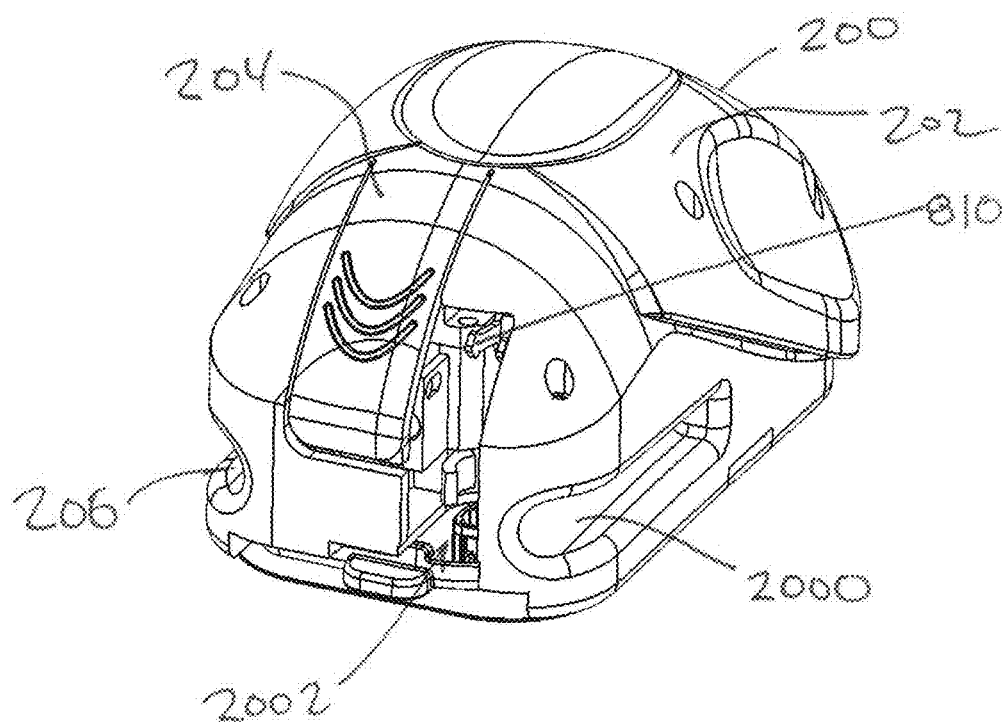
FIG. 20 shows a view of an inserter.
Figure 21:
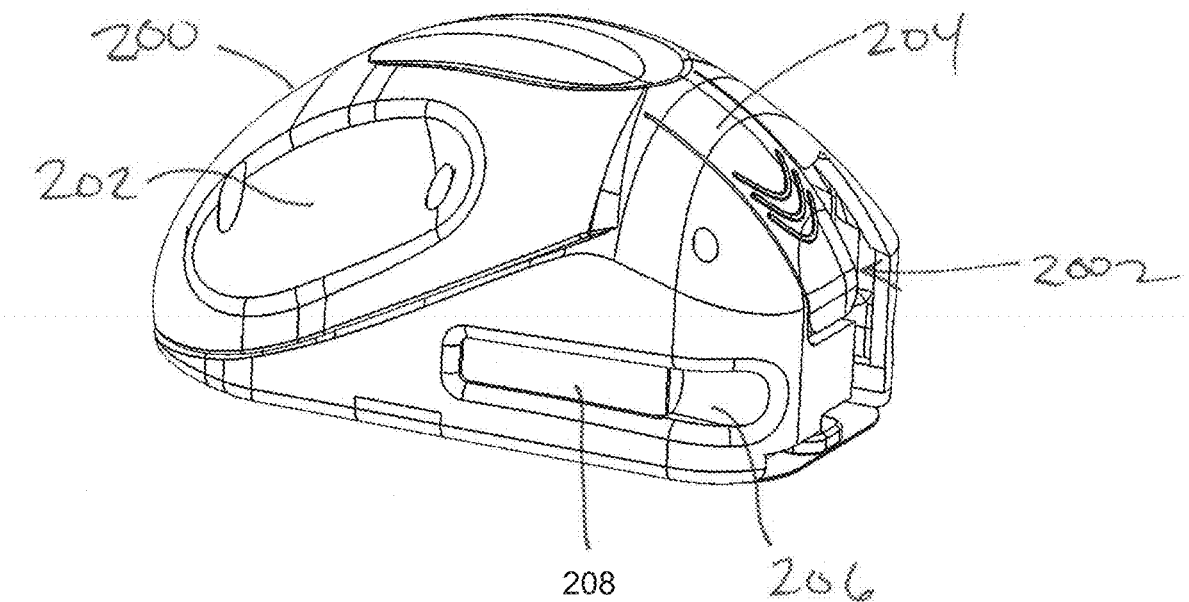
FIG. 21 shows a further view of an inserter.
Figure 22:
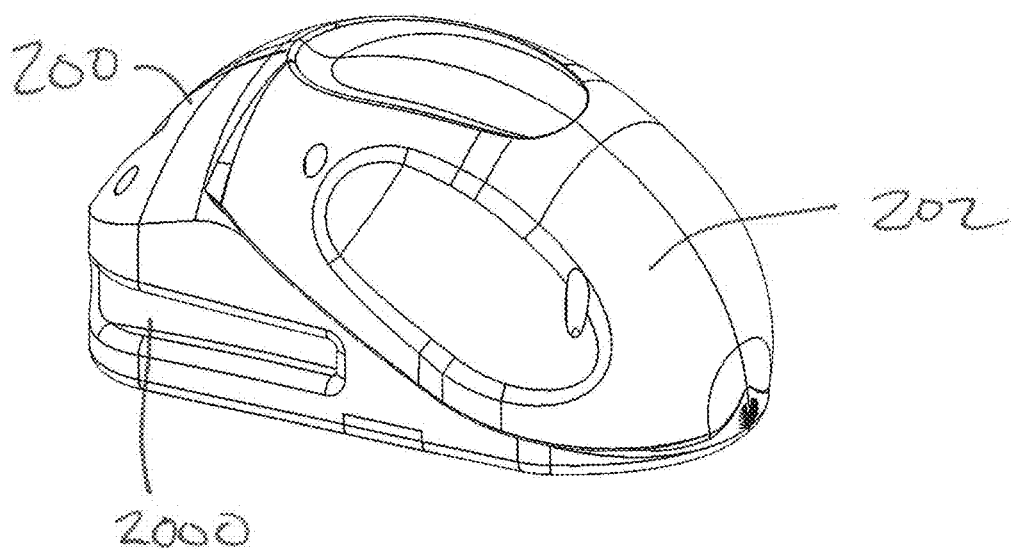
FIG. 22 shows a further view of an inserter.

FIGS. 20, 21, and 22 show further views of the inserter 200. In FIGS. 20 and 21 an additional guiding structure 2000 can be seen. It is able to mate with the supplementary guiding structure 108 shown in FIGS. 1A, 1B, and 1C. An opening 2002 for receiving the removable needle housing 114 is also seen. A portion of the needle driver 810 is also shown. The needle driver 810 is able to enter the slot 115 of the removable needle housing 114 to actuate the needle by pressing on the mechanism attachment point 1704.

FIG. 23 shows a cross sectional view of the inserter 200 that is mounted on a cradle 112. The box labeled 2300 shows a region which is enlarged in FIG. 24. FIG. 24 shows how the cradle 112 is mounted to the bottom of the inserter 200.

FIG. 25 illustrates how the removable needle 114 assembly interfaces with the inserter 200. In this FIG. the cradle 112 is shown as being mounted in the inserter 200. The removable needle assembly is moved away from both the cradle 112 and the inserter 200 for clarity. The needle drivers 810 pass through the slots 115 and be used for driving the insertion needle 1700 of FIG. 17. As the inserter 200 is slid onto the cradle, two gripping elements 2500 grip a gripping location 2502 of the removable needle assembly 114.

Figure 26:
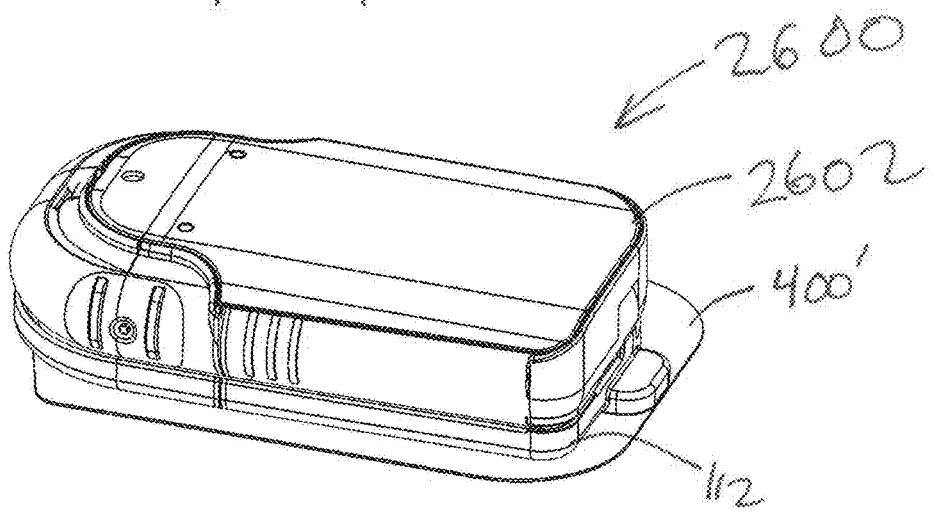
FIG. 26 shows an insulin pump mounted on a cradle.
Figure 27:
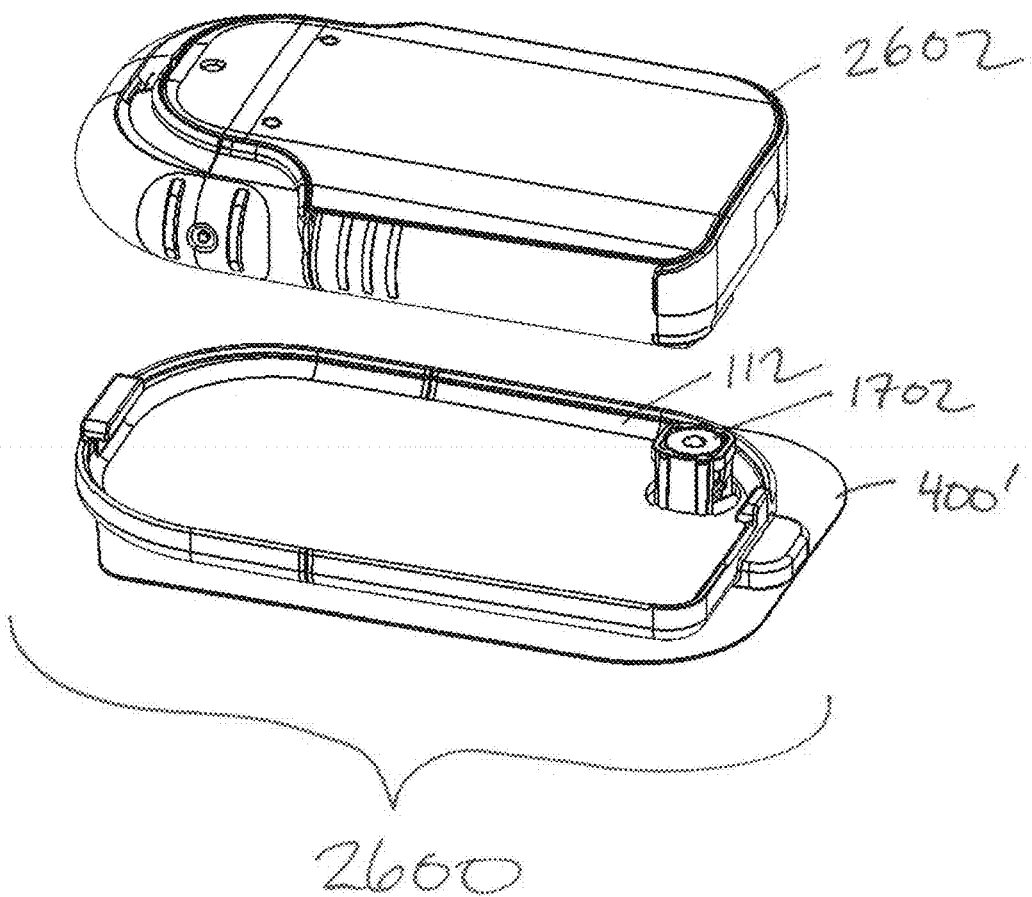
FIG. 27 shows an exploded view of the insulin pump and cradle of FIG. 26.

FIG. 26 and FIG. 27 show an assembly comprising the cradle 112 and an insulin pump 2602. In FIG. 26, the insulin pump is mounted on the cradle 112. In. FIG. 27, the insulin pump has been removed from the cradle. In FIG. 27, the cannula 1702 is shown as being inserted into a subject. The insulin pump 2602 is able to attach to the cannula 1702 to pump insulin into the subject.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS

| | |
|---|---|
| 100 | cartridge |
| 102 | opening |
| 103 | housing |
| 104 | interior volume |
| 105 | sealing surface |
| 106 | first guiding structure |
| 107 | first side wall |
| 108 | supplementary guiding structure |
| 109 | second side wall |
| 110 | guiding path |
| 112 | cradle |
| 114 | removable needle housing |
| 115 | slot |
| 116 | backing material |
| 118 | attachment point |
| 200 | inserter |
| 201 | medical system |
| 202 | cover |
| 202' | top cover |
| 202" | bottom cover |
| 203 | portion of inserter |
| 204 | button |
| 206 | second guiding structure |
| 208 | sliding element |
| 400 | surface of subject |
| 400' | adhesive layer |
| 700 | move at least a portion of the inserter into the interior volume of the housing along the guiding path |
| 702 | remove the inserter and the cradle from the interior volume |
| 704 | attach the cradle to the exterior surface of the subject |
| 706 | operate the insertion mechanism to actuate the insertion needle to insert the subcutaneous element into the subject |
| 708 | remove the inserter from the cradle |
| 800 | insertion mechanism |
| 802 | priming spring |
| 804 | retraction spring |
| 806 | drive spring or stored energy component |
| 808 | drive arm |
| 810 | needle driver |
| 812 | safety element |
| 814 | sloped surface |
| 816 | end point |
| 818 | connection point |
| 820 | release element |
| 1000 | sensing point |
| 1001 | mounting surface |
| 1002 | zoomed region |
| 1004 | release pin |
| 1100 | notched region |
| 1400 | curved surface |
| 1500 | zoomed region |
| 1700 | insertion needle |
| 1702 | cannula |
| 1704 | mechanism attachment point |
| 1800 | retracted position |
| 1900 | extended position |
| 2000 | additional guiding structure |
| 2002 | opening |
| 2300 | zoomed region |
| 2500 | gripping element |
| 2502 | gripping location |
| 2600 | assembly |
| 2602 | insulin pump |

What is claimed is:

1. A method of using a medical system having a cartridge and an inserter, the cartridge having a housing with an interior volume and a cradle removably disposed in the interior volume, the cradle comprising a subcutaneous element and an insertion needle, the method comprising:
    moving at least a portion of the inserter into the interior volume of the housing along a path guided by engagement of a guide of the housing with a corresponding guide of the inserter;
    completing the movement of the inserter into the interior volume to thereby cause the inserter to attach to the cradle;
    removing the inserter and the cradle from the interior volume; and
    operating the inserter to actuate the insertion needle to insert the subcutaneous element into a subject.

2. The method of claim 1, further comprising:
    attaching the cradle to an exterior surface of a subject; and
    removing the inserter from the cradle.

3. The method of claim 2, wherein the step of operating the inserter to actuate the insertion needle comprises releasing a stored energy source to drive the insertion needle into the subject and then withdrawing the insertion needle from the subject.

4. The method of claim 2, wherein the removing of the inserter from the cradle detaches the inserter from a needle housing.

5. The method of claim 1, wherein the guide of the housing engages a stored energy source of the inserter during the step of moving the inserter into the interior volume, whereby the stored energy source is primed during the insertion of the inserter into the interior volume of the housing.

6. The method of claim 5, wherein the stored energy source comprises a sliding member positioned with the guide of the inserter and the moving the inserter into the interior volume causes the sliding member to slide relative to the guide of the inserter, whereby the stored energy source is primed during the insertion of the inserter into the interior volume of the housing.

7. The method of claim 1, wherein, during the removing of the inserter and the cradle from the interior volume, a backing material is removed from the cradle, thereby exposing an adhesive layer on a skin contact side of the cradle.

8. The method of claim 1, wherein the step of removing the inserter and the cradle from the interior volume takes place before the step of operating the inserter.

9. The method of claim 1, wherein the step of removing the inserter and the cradle from the interior volume includes removing the subcutaneous element and the insertion needle therewith.

10. The method of claim 1, wherein step of removing the inserter and cradle from the interior volume comprises moving the inserter and cradle as a single unit.

* * * * *